United States Patent [19]
Mori et al.

[11] Patent Number: 5,824,856
[45] Date of Patent: Oct. 20, 1998

[54] PROCESS FOR PRODUCTION OF EXOGENOUS GENE OR ITS PRODUCT IN PLANT CELLS

[75] Inventors: Masashi Mori; Kazuyuki Mise; Tetsuro Okuno; Iwao Furusawa, all of Kyoto, Japan

[73] Assignee: Nihon Nohyaku Co., Ltd., Tokyo, Japan

[21] Appl. No.: 663,164

[22] Filed: Mar. 1, 1991

[30] Foreign Application Priority Data

Sep. 7, 1990 [JP] Japan ..................................... 2-238234

[51] Int. Cl.⁶ .............................. C12N 5/00; C12N 15/00
[52] U.S. Cl. .................. 800/205; 435/172.3; 435/320.1; 435/419
[58] Field of Search .......................... 800/205; 435/69.1, 435/172.3, 320.1, 375, 419

[56] References Cited

U.S. PATENT DOCUMENTS

| | | | |
|---|---|---|---|
| 5,418,153 | 5/1995 | Mori et al. | 435/172.3 |
| 5,466,788 | 11/1995 | Ahlquist et al. | 435/172.3 |

FOREIGN PATENT DOCUMENTS

| | | |
|---|---|---|
| 546542 | 7/1984 | Australia . |
| 586041 | 5/1987 | Australia . |
| 626473 | 5/1991 | Australia . |
| 64-80281 | 3/1989 | Japan . |
| WO8301176 | 4/1983 | WIPO . |

OTHER PUBLICATIONS

French, R., et al. Science, vol. 231, (1986) pp. 1294–1297.
van Dun, C.M.P., et al. Virology, vol. 163 (1988) pp. 572–578.
D. Taschner et al., Virology 181:445–450 ('91).
R.M. Leiser et al., Kulyurpflanz 38:81–90 ('90).
J. Bujarski et al. EMBO J. 5(8) 1769–74 ('86).
R. French et al. Science 231:1294–97 ('86).
W. Miller et al. Nature 316:68–70 ('85).
A. Dzianott et al. PNAS 86:4823–7 '89.
Fromm et al. Nature (1986) vol. 319, pp. 791–793.
Shillito et al. BiolTechnology (1985) vol. 3, pp. 1099–1103.
Takamatsu et al, "Expression of bacterial chloramphenicol acetyltransferase gene in tobacco plants mediated by TMV–RNA", The EMBO Journal, vol. 6, No. 2, pp. 307 and 310.

*Primary Examiner*—Bruce R. Campbell
*Attorney, Agent, or Firm*—Pillsbury, Madison & Sutro, IP Group of Cushman, Darby & Cushman

[57] ABSTRACT

A process for production of an exogenous gene or its product in a plant cell which comprises: inserting into a genome of plant, i) cDNA of replicase gene from an RNA plant virus, and
  ii) cDNA of a recombinant virus genomic RNA in which coat protein gene is wholly or partly replaced with desired exogenous gene, or inoculating said recombinant virus genomic RNA on a plant cell having cDNA of replicase gene inserted in the genome. The process of the present invention enables to efficiently produce the desired exogenous gene product in plant cells in large quantities.

19 Claims, 10 Drawing Sheets

PROCESS FOR PRODUCTION OF EXOGENOUS GENE OR ITS PRODUCT IN PLANT CELLS

BACKGROUND OF THE INVENTION

1. Field of the Invention

An object of the present invention is to provide a process for producing useful substances in plant cells in agricultural and pharmaceutical fields, by producing large quantities of an exogenous gene or its products in plant cells capable of producing replicase of RNA plant virus, e.g., brome mosaic virus (hereafter referred to as BMV), by genetic engineering technique. Another object of the present invention is to create transformed plants capable of expressing useful characters. The present invention also relates to vectors for plant transformation and vectors capable of producing recombinant RNA as well as transformed plant cells.

2. Related Art Statement

As a technique for producing useful polypeptide in plant cells or as a method for imparting useful characters, for example, plant virus resistance, to plants by the useful polypeptide, development on a method for introducing and expressing an exogenous gene in a plant genome using the Ti plasmid transformation system and on a method for utilizing multiplication system of plant virus is under way. It is known that in the case of introducing a coat protein gene of tobacco mosaic virus (TMV) into a plant genome using the Ti plasmid transformation system, an amount of coat protein produced is at most 0.01% of the total plant protein (Beachy et al., (1990), Annu. Rev. Phytopathol., 28: 451–474). According to this technique, an amount of the product produced by an exogenous gene is dependent on a promoter activity which regulates an amount of transcription so that survey of a promoter capable of imparting a more potent transcription activity becomes necessary. On the other hand, TMV can produce 2 g/kg of leaves in a host plant at the maximum. In the case of a method utilizing the multiplication system of a plant virus which comprises replacing the exogenous gene of a desired substance for the gene moiety of TMV coat protein and inoculating the resulting recombinant on a host plant, however, an amount of the desired substance produced was about 1 mg/kg of leaves (Takamatsu et al., (1987) EMBO J., 6: 307–311). Turning to a problem involved in TMV, 3 kinds of genes are encoded overlapping on one single stranded RNA in TMV. It is thus considered that by replacement of an exogenous gene, its regulating mechanism of TMV replication would be affected. For this reason, it has also been investigated to utilize plant viruses having a plant genome divided on several kinds of single stranded RNAs.

As an example, there is BMV which uses as a host many plants belonging to the family Gramineae and falls under the bromo virus group. The genome of BMV is composed of 3 kinds of (+) single stranded RNAs and these RNAs are called RNAs 1, 2 and 3, by priority of a large molecular weight. In addition, RNA4 called subgenomic RNA also exists in BMV (FIG. 1). These RNAs are enclosed in spherical particles having a diameter of about 26 nm, RNAs 1 and 2 being alone, respectively and RNAs 3 and 4 being together (Lane et al., (1974) Adv. Virus Res., 19: 151–220). BMV has characteristics that an amount of BMV multiplicated in infected plant cells is large and the genome is divided. It is thus considered that its regulating mechanism of virus replication would be affected only with difficulty by replacement of the exogenous gene in coat protein gene and hence, BMV has been studied as a material for producing substances using molecular biology techniques. The nucleotide sequence of the entire genome of BMV has already been clarified (Ahlquist et al., (1984) J. Mol. Biol., 172: 369–383); RNA1 has 3234 bases in the full length and encodes 1a protein (molecular weight of 109 kilodaltons (KD)), RNA2 has 2865 bases in the full length and encodes 2a protein(molecular weight of 94 KD), and 1a and 2a proteins are considered to be subunits of replicase. It is thought that in (+)-stranded BMV RNA, (−)-strand would be synthesized from (+)-strand in a plant cell by this replicase and using the synthesized (−)-strand as a template, (+)-strand would be synthesized in large quantities. On the other hand, RNA3 has 2134 bases in the full length and encodes the two genetic products of 3a protein (molecular weight of 34 KD) and coat protein (molecular weight of 20 KD) but only the 3a protein encoded on the 5' side is directly translated from RNA3. RNA4 has 876 bases in the full length, possesses the same sequence as that of the coat protein gene portion of RNA3, and becomes mRNA of coat protein. RNA4 is synthesized from RNA3 in a host cell (Ahlquist et al., (1981) J. Mol. Biol., 153: 23–38). Its mechanism reveals that (−)-strand is synthesized from (+)-stranded RNA3 and (+)-stranded RNA4 is synthesized from the inside of this (−)-strand (Miller et al., (1985) Nature, 313: 68–70). Ahlquist et al. succeeded in expressing chloramphenicol acetyl transferase (CAT) on a high level, by removing the most of the coat protein gene from RNA3, introducing CAT gene at the removed site, and infecting the resulting recombinant RNA3 to barley protoplast together with RNAs 1 and 2. However, they failed to utilize this technique in expression of CAT gene on a plant level (French et al., (1986) Science, 231: 1294–1297).

As a result of investigations on BMV gene to provide a more excellent method for production, the present inventor has accomplished this invention.

OBJECTS OF THE INVENTION

As stated above, investigations have been made on a method for expressing an exogenous gene in a plant cell in large quantities. In the prior art, there was no report on expression of an exogenous gene in a plant cell either by inserting cDNA of replicase gene of plant virus and CDNA of virus genomic RNA carrying coat protein gene into a plant genome independently, or by inoculating recombinant virus genomic RNA on a plant cell having cDNA of replicase gene of plant virus inserted into a plant genome. For example, in the case of constructing a vector from a virus that the virus genome represented by BMV, cucumber mosaic virus (hereinafter referred to as CMV) and alfalfa mosaic virus (hereafter referred to as AMV) is divided into 4 RNA chains, BMV has been most extensively studied. However, there is no report that each gene of BMV is inserted into a plant genome and expressed there. Recombinant RNA3 in which the coat protein gene has been replaced with an exogenous gene is merely mixed with RNAs 1 and 2 and the mixture is inoculated on a plant protoplast to produce the exogenous gene in the protoplast (FIG. 9-1). Since an infection efficiency of RNA to the protoplast is poor and the recombinant virus RNA cannot be systemically infected, a problem arises that the expression amount in each cell is small. Furthermore, this technique cannot be utilized for obtaining a genetically transformed plant. Moreover, production of virus RNA in vitro is a serious drawback in industrialization in view of costs. Accordingly, there has been a need for the development of a method using genetic engineering technique which comprises constructing genomic RNA cDNA of RNA plant virus including BMV and recombinant cDNA having replaced the coat protein gene of virus genomic RNA cDNA with an exogenous gene, modifying them to express as virus RNA in a plant cell, and inserting them into the genome of a plant by the plant cell transformation method such as Ti plasmid, etc. or by the DNA direct introduction method such as electroporation, etc. Thus, virus replicase is produced in all cells and recombinant RNA containing the exogenous gene is replicated to express mRNA of the exogenous gene in large quantities (FIG. 9-2). In this case, multiplication of virus RNA in large amounts leaves plants to cause disease symptom and adversely affects the growth of plants. Therefore, multiplication of virus RNA other than the exogenous gene is not considered to be necessarily required. There has thus been a need for the development of a method for modifying virus genome to delete of the ability of multiplying RNAs 1 and 2 in the case of genomic RNA containing virus replicase gene, for example, BMV, and as the result, translate 1a and 2a protein (BMV replicase) alone.

SUMMARY OF THE INVENTION

The present invention relates to a process which comprises inserting RNA replicase gene of RNA plant virus into a genome of a plant cell and synthesizing mRNA of a desired exogenous gene by virus replicase produced in a plant cell in large quantities to produce polypeptide as its genetic product in large quantities. The present invention also relates to a method for constructing a plant having a useful character by producing polypeptide affecting the character of a plant or antisense RNA in a plant cell in large quantities.

That is, an object of the present invention is to provide a process for production of an exogenous gene or its product in a plant cell which comprises inserting into a genome of a plant cell, cDNA of replicase gene from an RNA plant virus and cDNA of a recombinant virus genomic RNA in which coat protein gene is wholly or partly replaced with a desired exogenous gene (hereafter referred to as recombinant virus genomic RNA), or inoculating said recombinant virus genomic RNA on a plant cell having cDNA of replicase gene inserted in a plant genome.

Another object of the present invention is to provide a DNA molecule containing a promoter which functions in a plant cell, cDNA of RNA replicase gene of a plant virus and a terminator which functions in a plant cell.

A further object of the present invention is to provide a transcription vector comprising an in vitro functional promoter and cDNA of virus genomic RNA and capable of producing recombinant virus genomic RNA.

A still further object of the present invention is to provide a plant obtained by regeneration of a transformed plant cell containing the DNA molecule in a geneme of a plant cell.

PKT: NOS promoter, kanamycin resistant gene and NOS terminator

35 : CaMV35S promoter

T: CaMV terminator

▸: T-DNA boader sequence of Ti plasmid

■: cDNA corresponding to the non-translated region of BMV RNA

▨: cDNA corresponding to the translated region of BMV RNA

⌐: transcription initiation site and direction of the transcription

Figure 3:
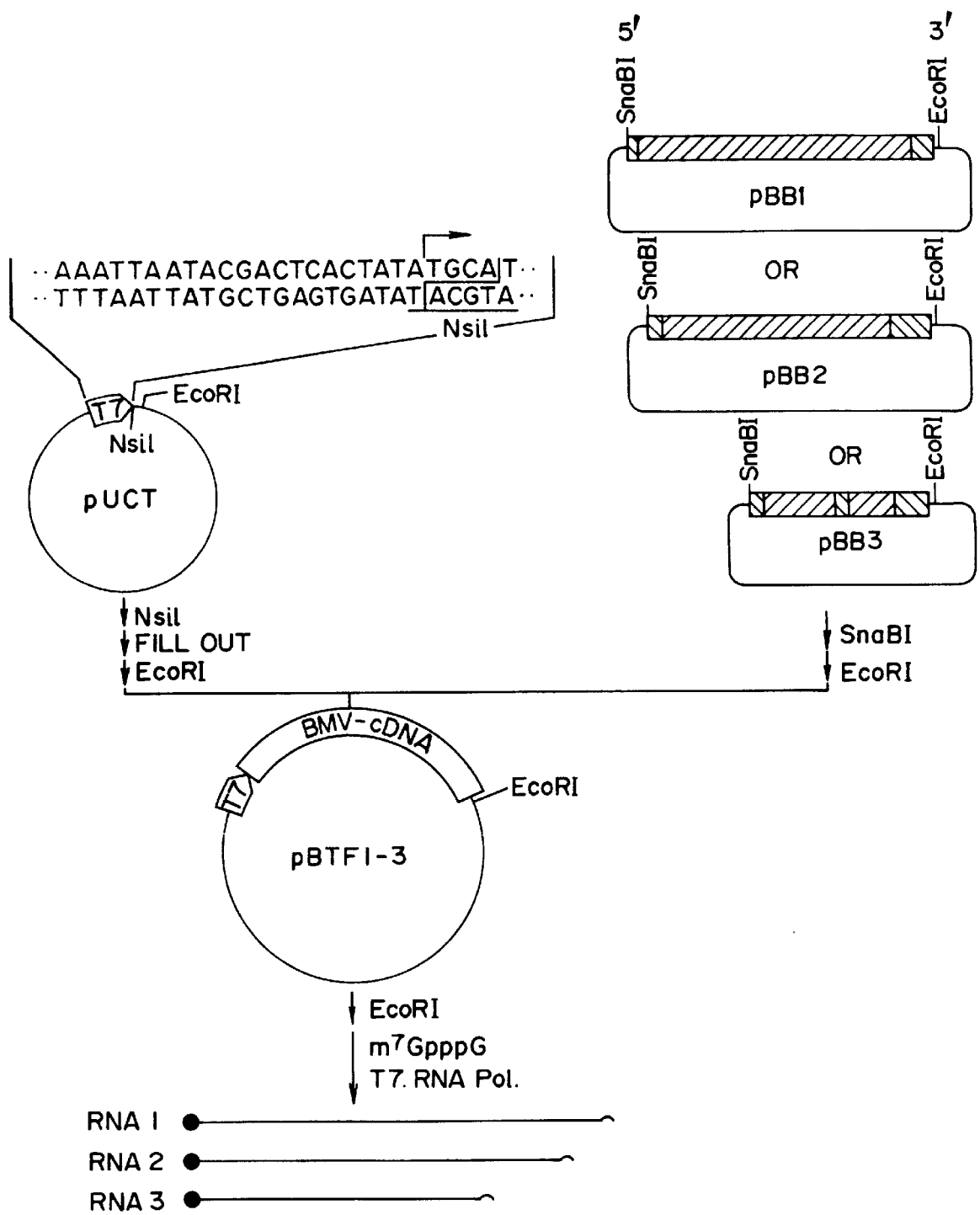
Figure 4:
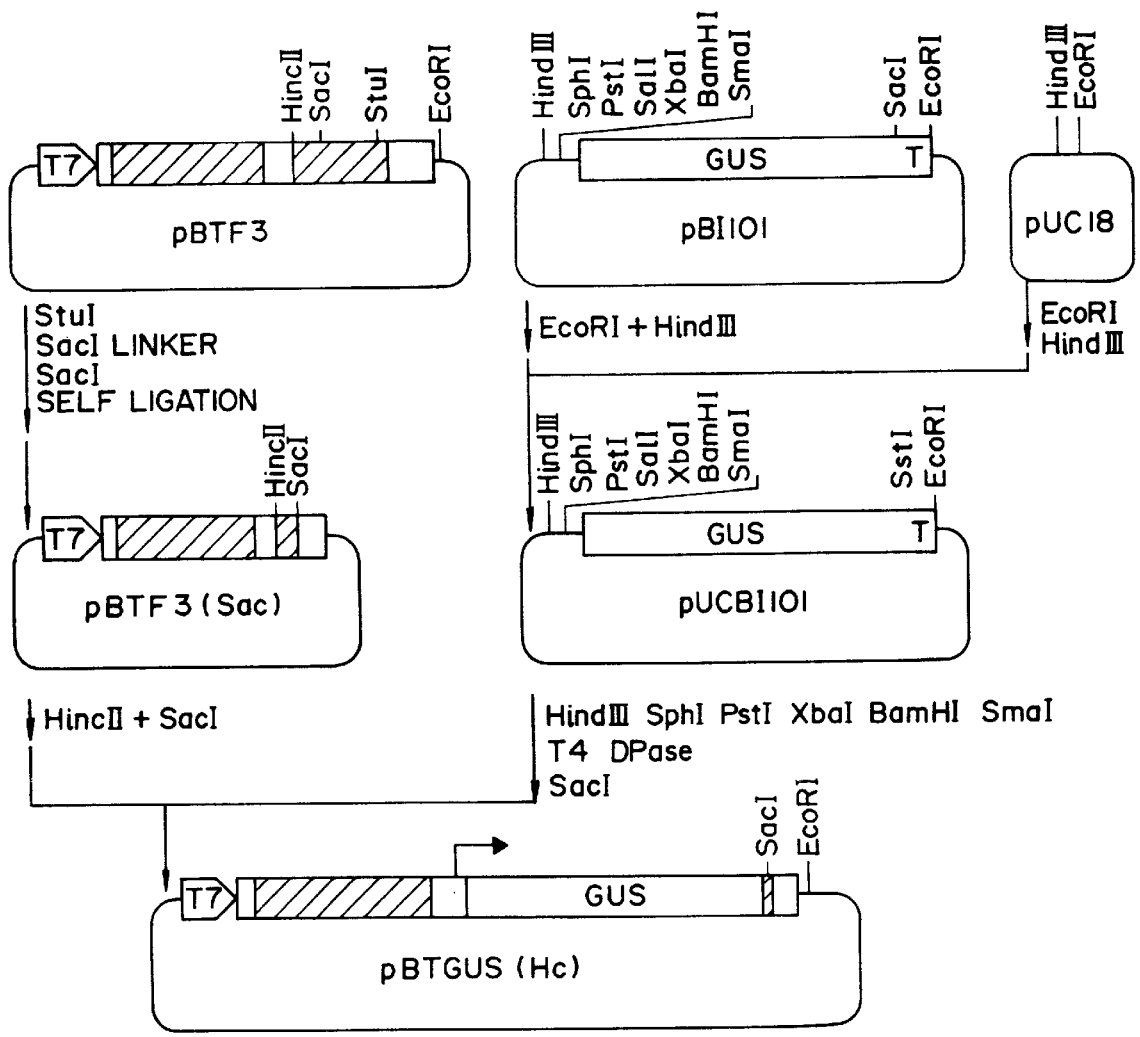

Type (1): transformation vector in which the full length cDNA of BMV RNA has been inserted Type (2): transformation vector in which cDNA of BMV RNA deleted of the 3' non-translated region alone has been inserted FIG. 3 shows introduction of completely full length cDNA of BMV (see SEQ ID NOS: 4 and 5) RNA into transcription vector and the synthesis of BMV RNA in vitro using T7 RNA polymerase T7: T7 promoter ⌐: transcription initiation site and direction of the transcription $m^7GpppG$: cap analog ●: cap structure ⌒: superfluous nucleotide added to 3' of BMV RNA FIG. 4 shows construction of transcription vector of recombinant RNA3 in which BMV coat protein gene has been replaced with GUS gene.

□: cDNA corresponding to the non-translated region of BMV RNA

▨: cDNA corresponding to the translated region of BMV RNA

T7: T7 promoter

⌐: synthesis initiation site of BMV RNA4 and direction of the synthesis

Figure 5:
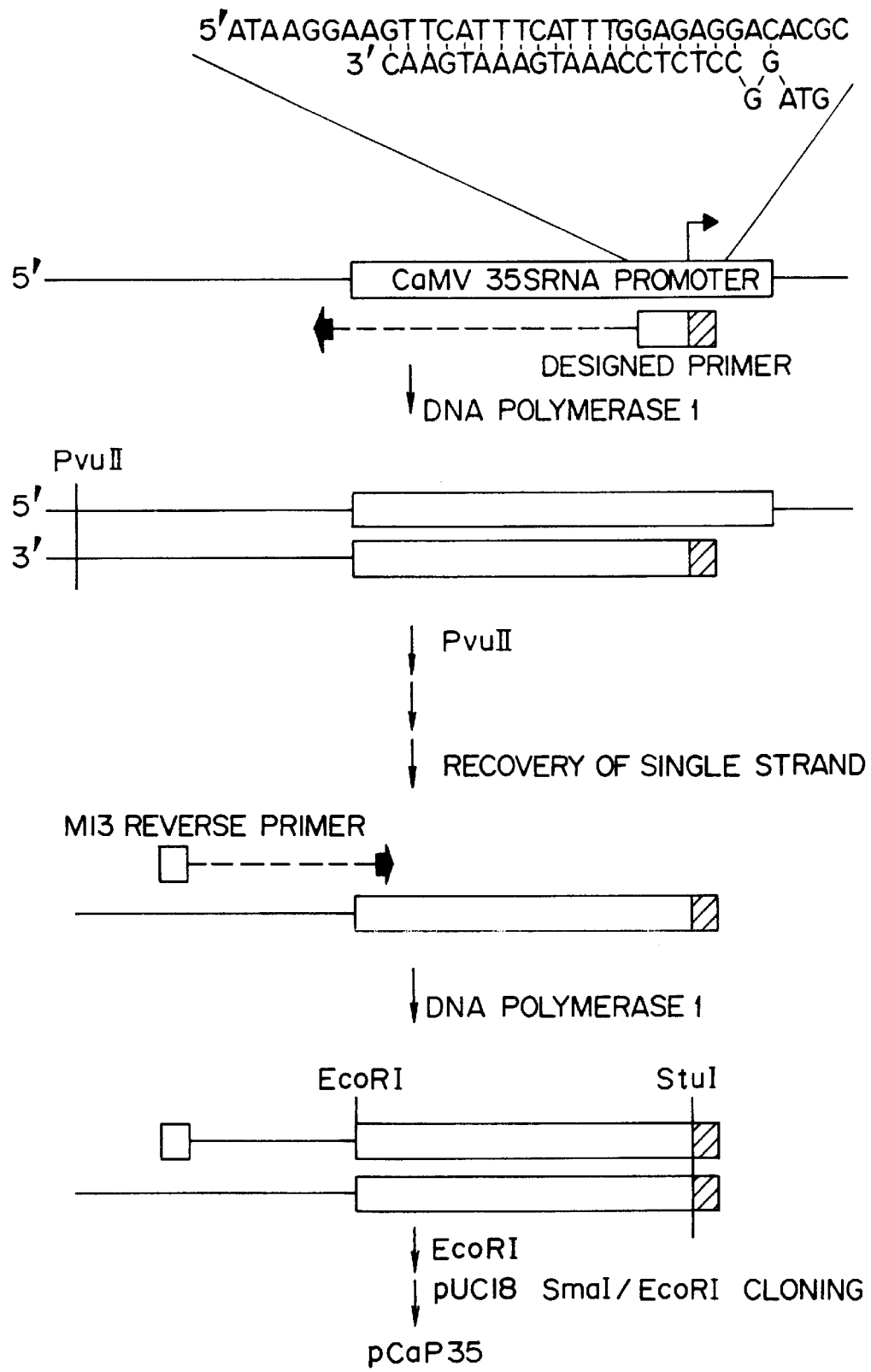

FIG. 5 shows a process for introducing the restriction enzyme site (StuI) into the transcription initiation site of CaMV35S promoter by site-directed mutagenesis (see SEQ ID NOS: 6 and 7).

▨: mutated nucleotide sequence

⌐: transcription initiation site and direction of the transcription

Figure 6:
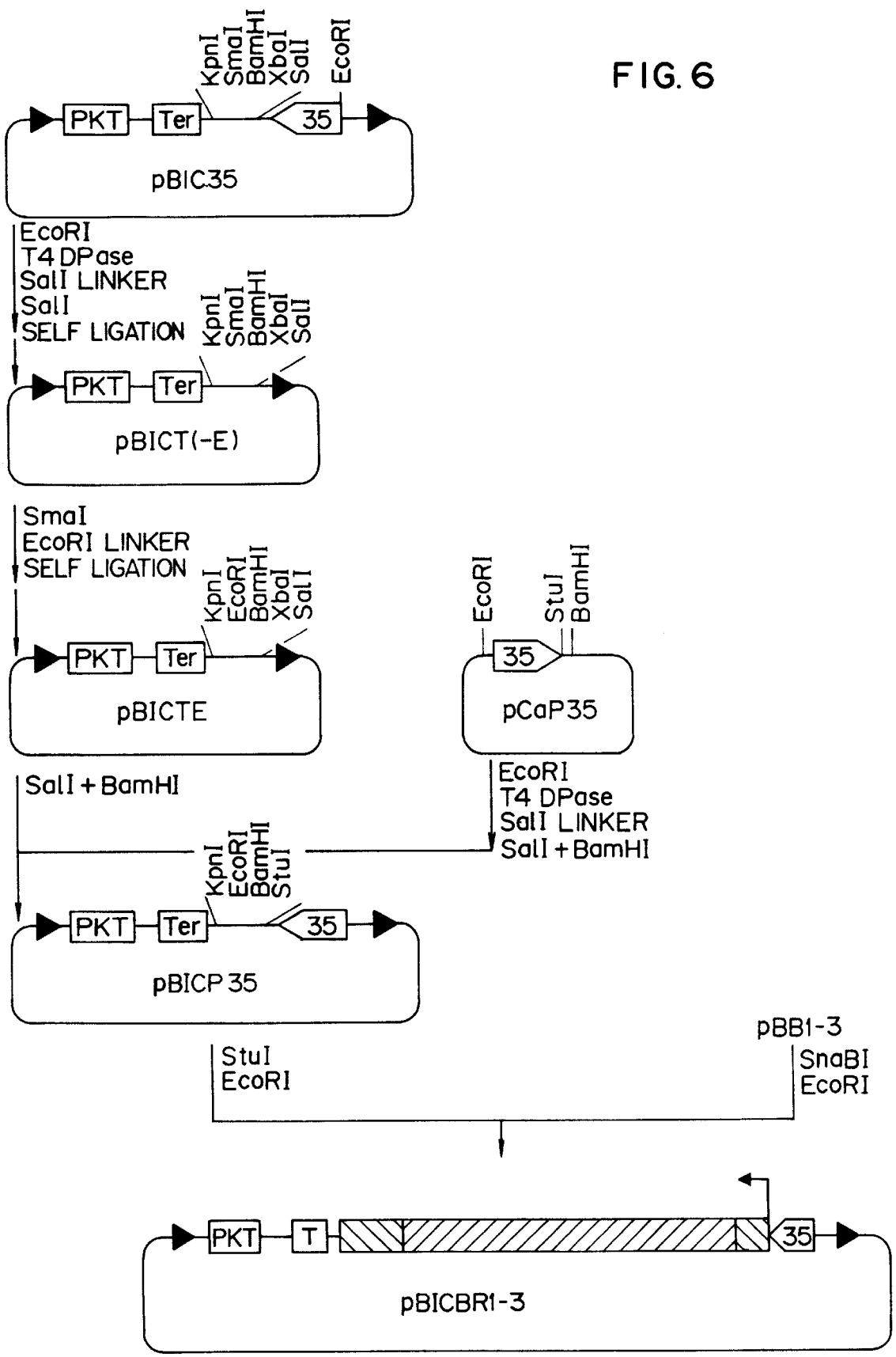

FIG. 6 shows construction of transformation vector pBICBR1–3 in which the full length cDNA of BMV RNA has been introduced.

PKT: NOS promoter, kanamycin resistant gene and NOS terminator

35: CaMV35S promoter

T : CaMV terminator

▸: T-DNA boader sequence of Ti plasmid

■:cDNA corresponding to the non-translated region of BMV RNA

▨: cDNA corresponding to the translated region of BMV RNA

⌐: transcription initiation site and direction of the transcription

Figure 1:
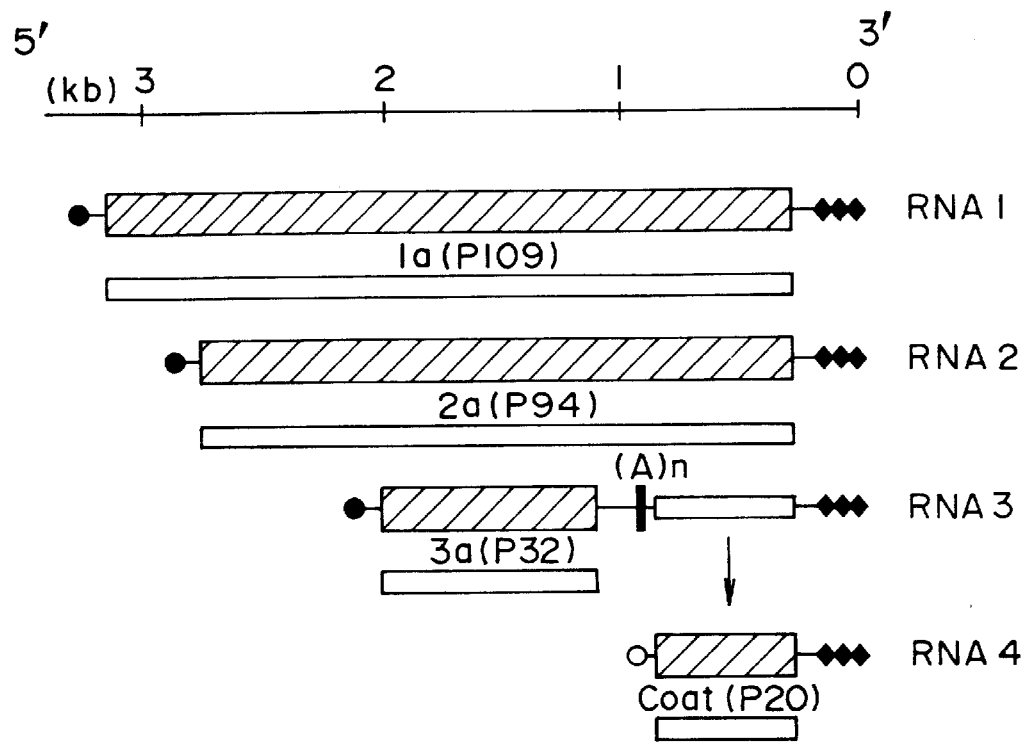
FIG. 1 shows a mode for gene expression of BMV.
Figures 1, 7:
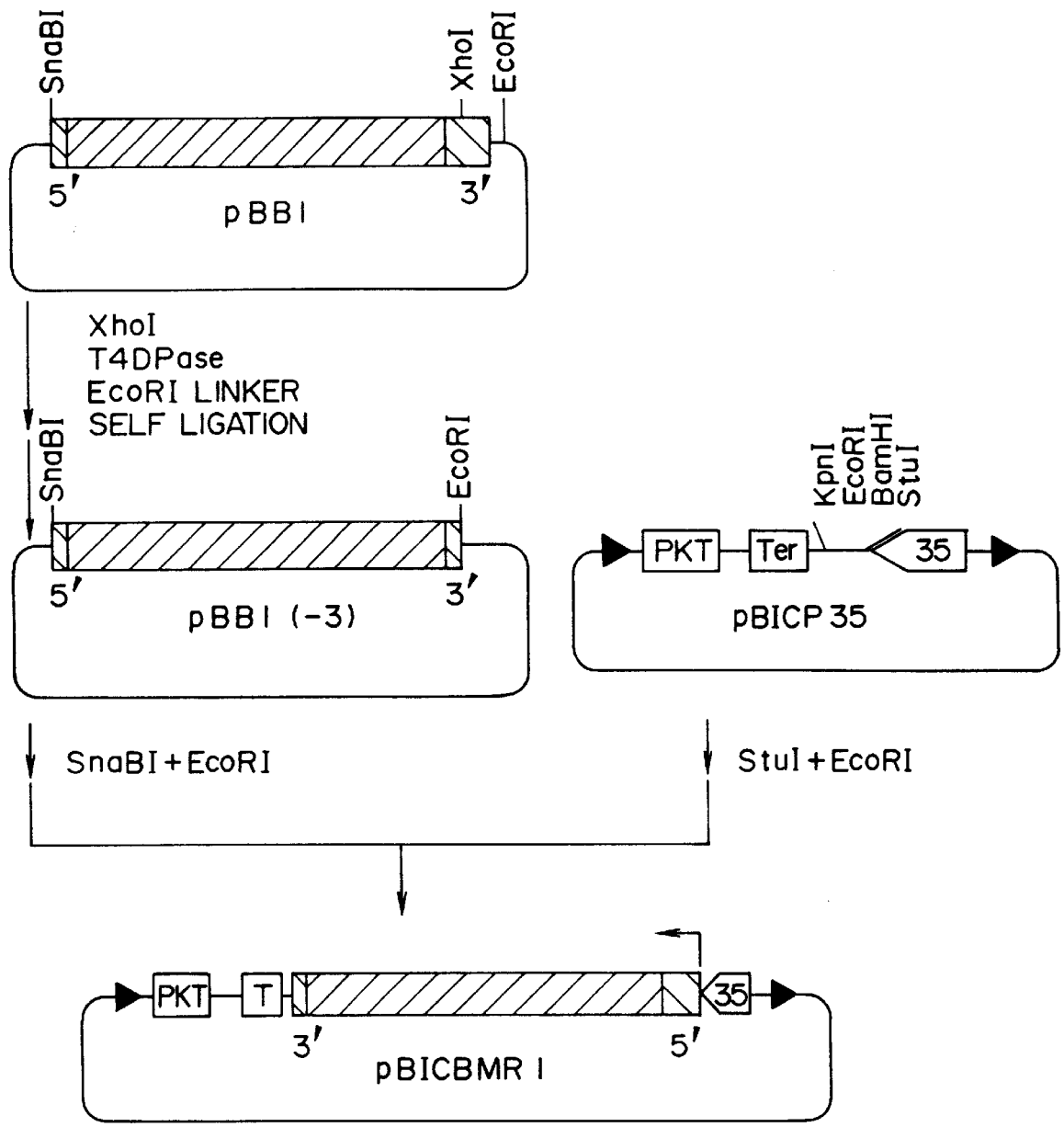
Figures 2, 7:
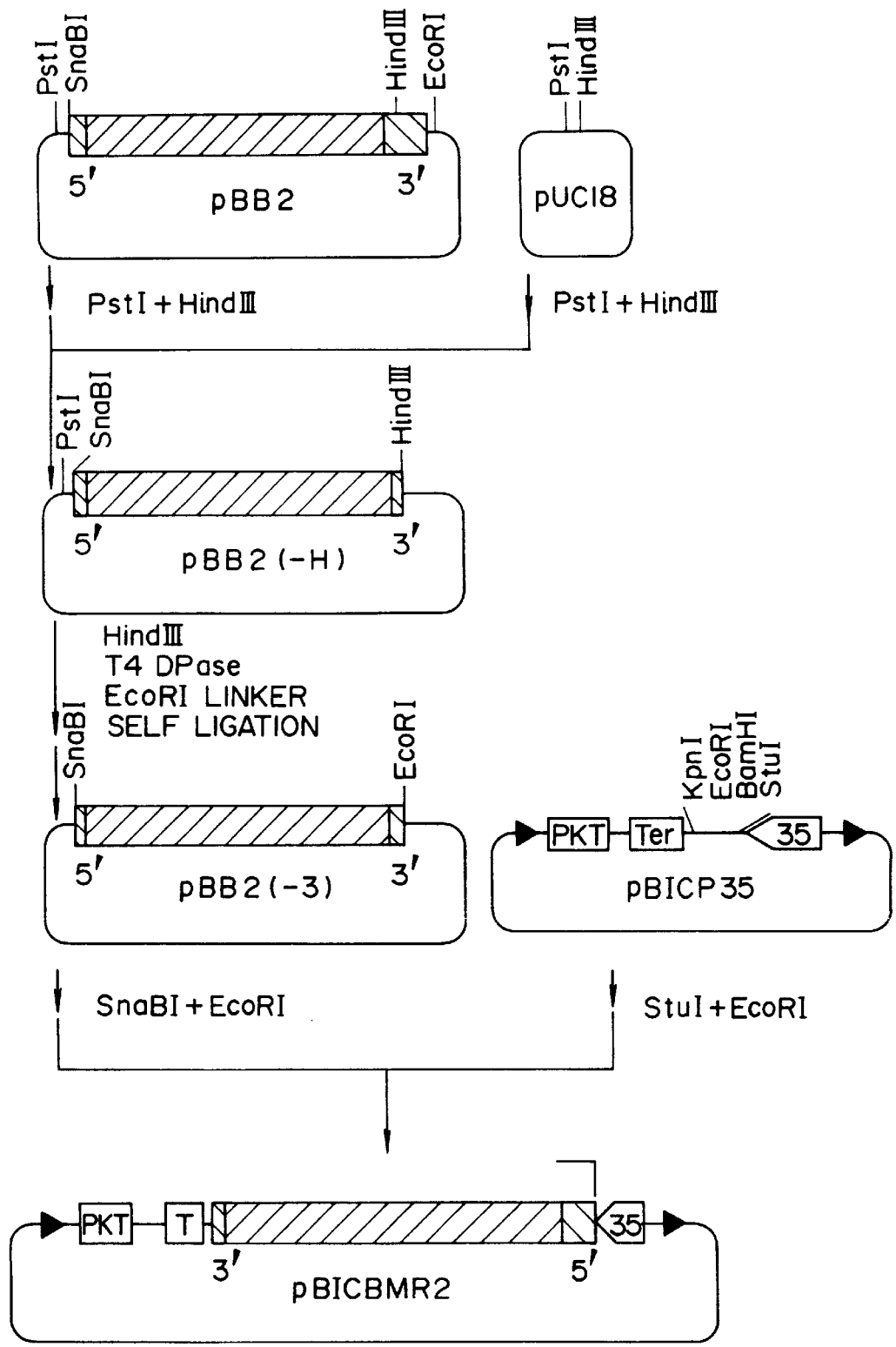
Figures 3, 7:
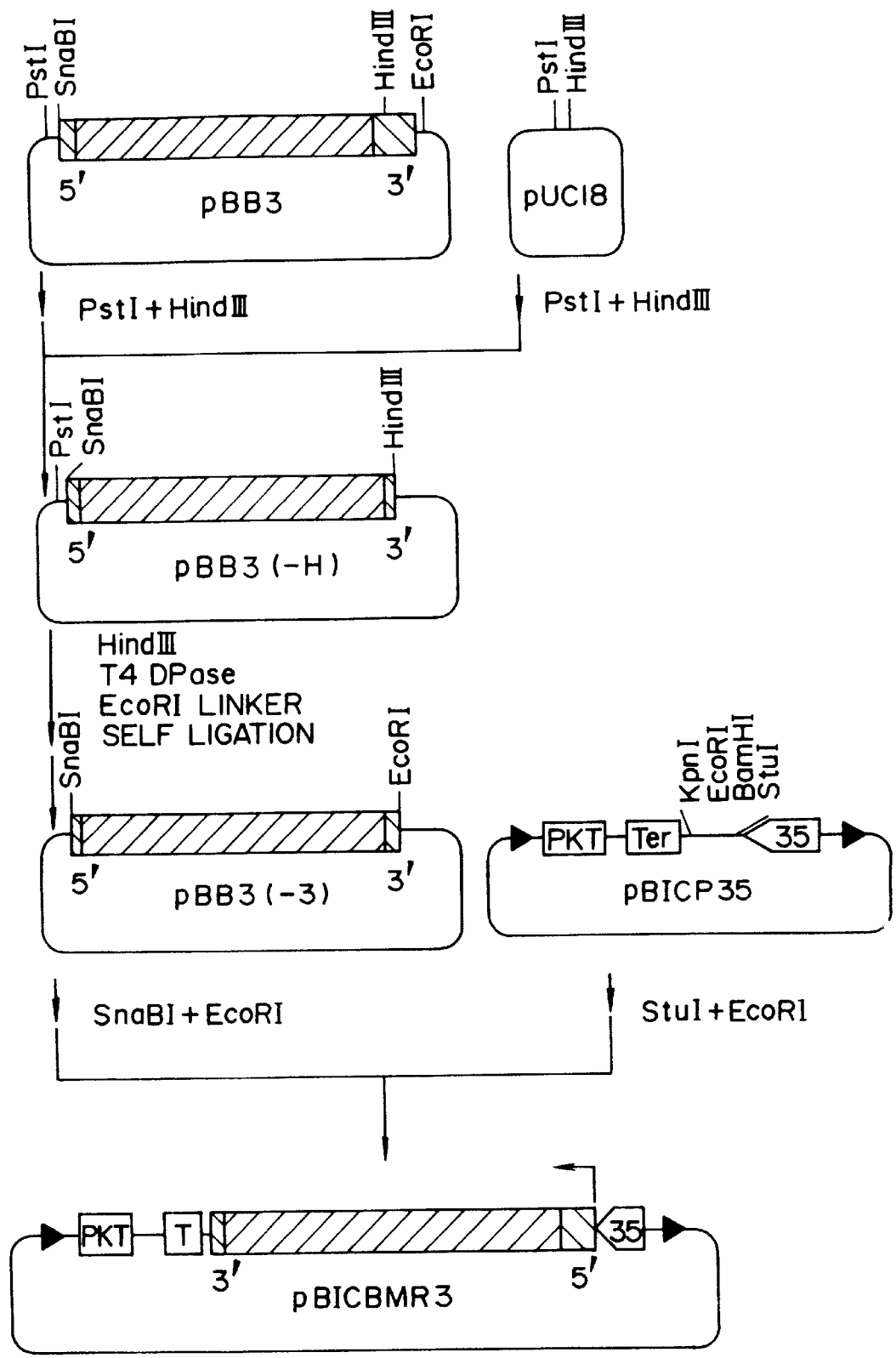

FIGS. 7-1–7-3 show construction of transformation vector pBICMBR 1, 2 and 3 in which cDNA of BMV RNA having deletion at the 3' non-translated region.

PKT: NOS promoter, kanamycin resistant gene and NOS terminator

35: CaMV35S promoter

T : CaMV terminator

▸: T-DNA boader sequence of Ti plasmic

□: CDNA corresponding to the non-translated region of BMV RNA

▨: CDNA corresponding to the translated region of BMV RNA

⌐: transcription initiation site and direction of the transcription

Figure 8:
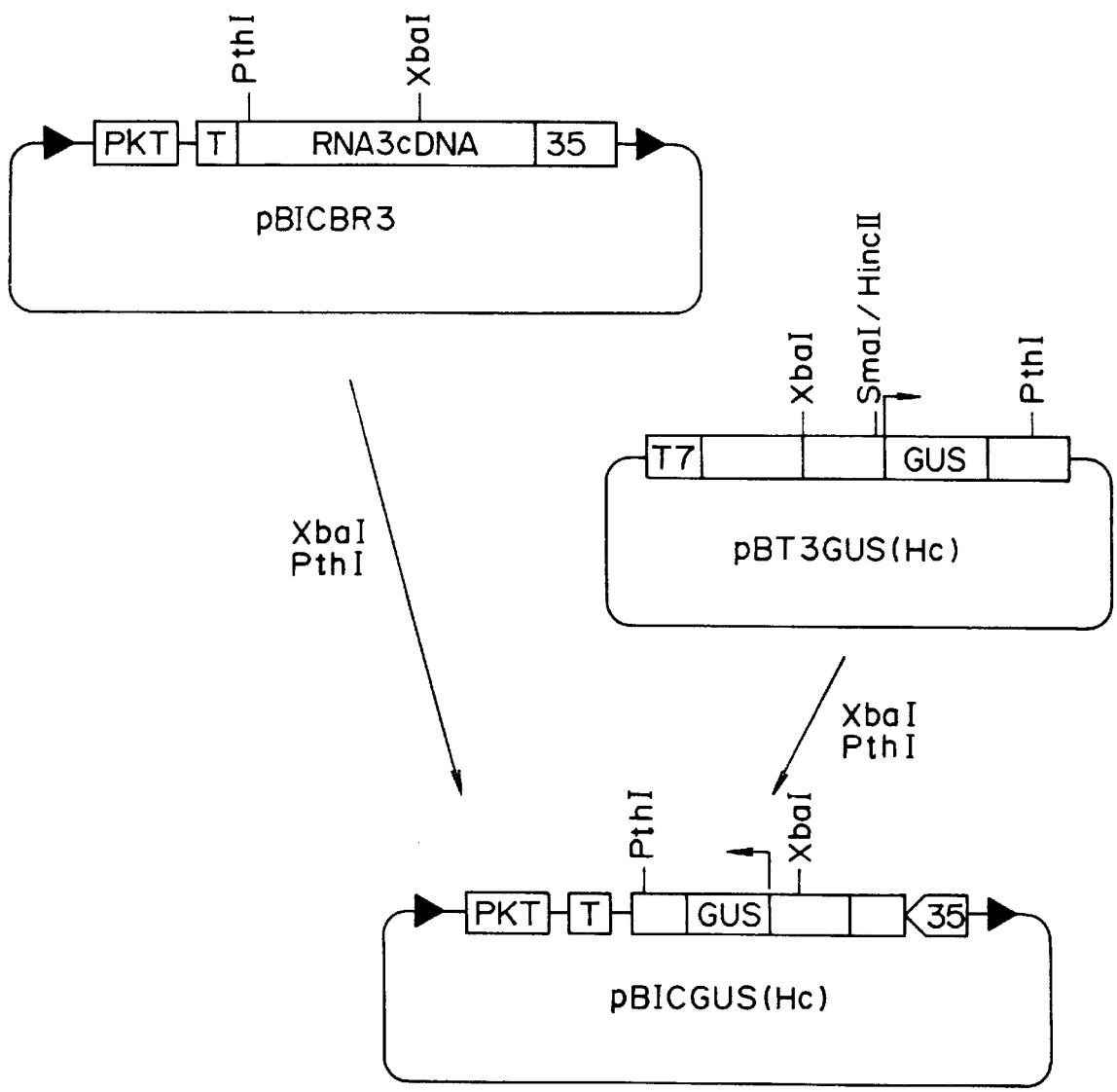

FIG. 8 shows construction of transformation vector pBIC3GUS(Hc) in which BMV coat protein gene has been replaced with GUS gene.

PKT: NOS promoter, kanamycin resistant gene and NOS terminator
35: CaMV35S promoter
T : CaMV terminator
T7: T7 promoter
↑: synthesis initiation site of BMV RNA4 and direction of the synthesis.

Figure 2:
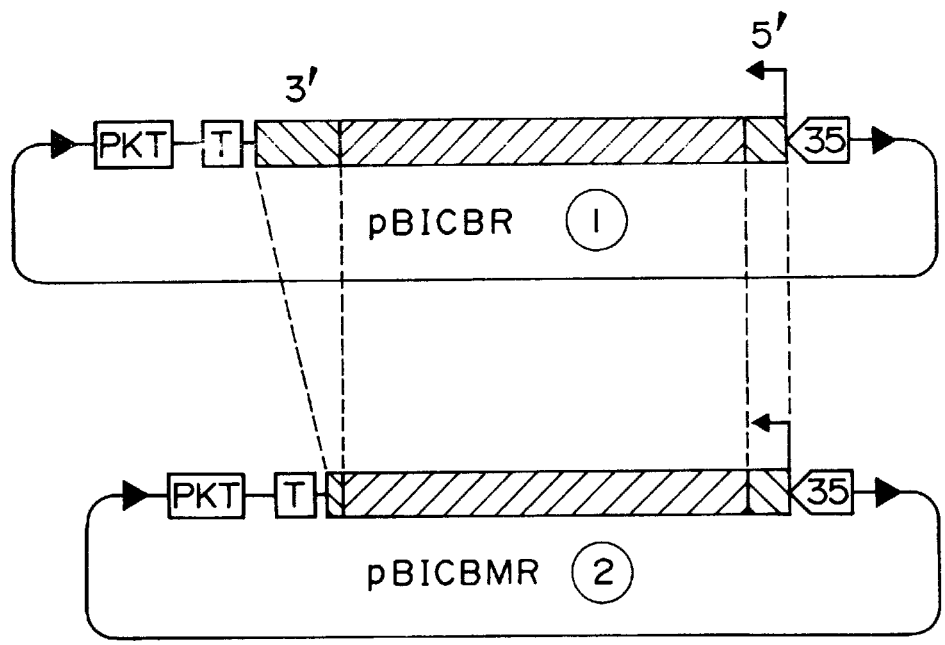
FIG. 2 shows a tobacco transformation vector in each gene of BMV.
Figures 2, 9:
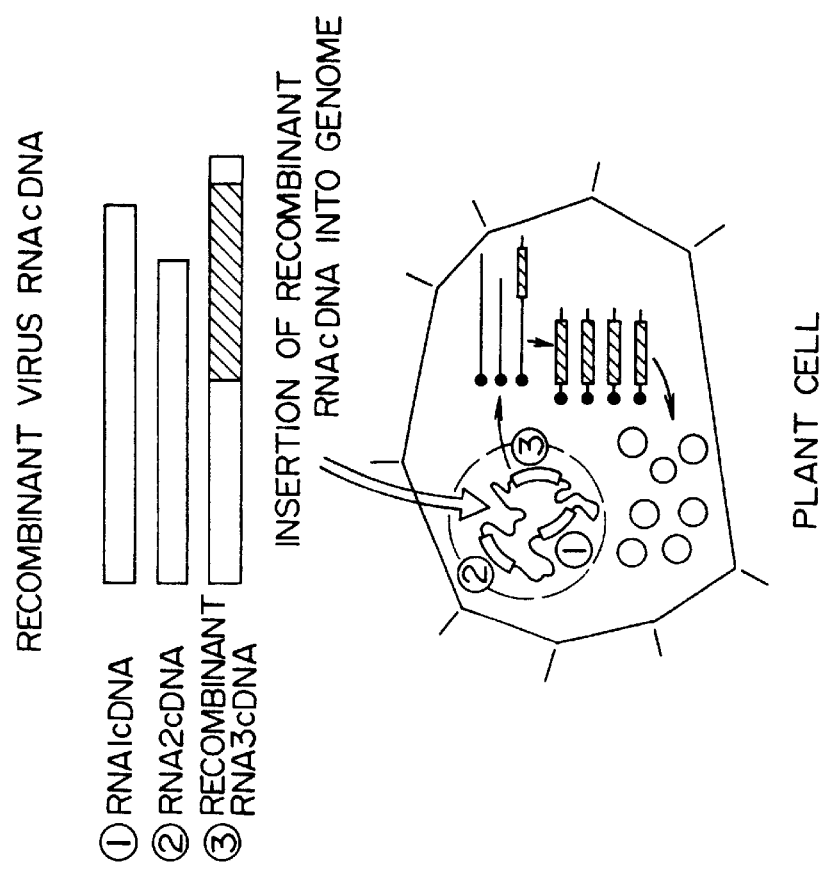
Figures 1, 9:
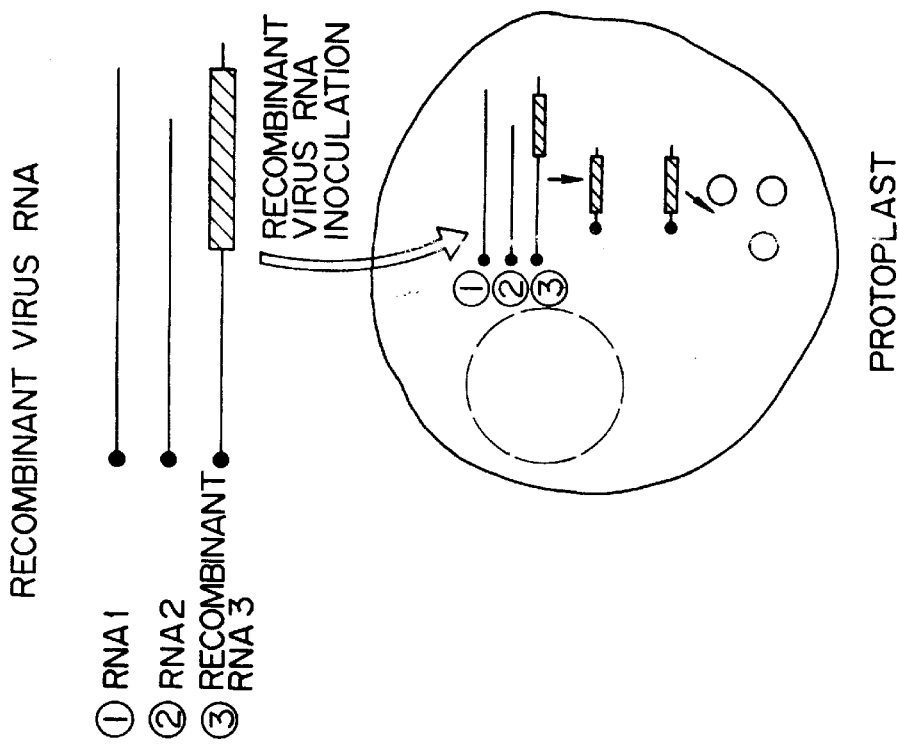

FIGS. 9-1 and 9-2 represent a schematic illustration showing a method for production of a desired polypeptide.

DETAILED DESCRIPTION OF THE PREFERRED EMBODIMENTS (1) RNA plant virus

The RNA plant virus which can be used in the present invention is preferably composed of (+)-stranded RNA where virus genes are present, more preferably BMV, CMV and AMV. The genomic RNA cDNAs containing the replicase genes of these viruses are inserted into a genome of a plant cell. The genomic RNA cDNAs containing the coat protein gene in which the exogenous gene has been incorporated are inserted into a genome of a plant cell or inoculated as RNA synthesized in vitro. In the case of BMV, CMV and AMV, the genome consists of 4 kinds of RNAs (FIG. 1) and these viruses are handled most easily. Even in other viruses, as far as the replicase gene and the coat protein gene can be inserted into a genome of a plant cell such that each of these gene can be expressed independently, the present invention can apply to such viruses.

Taking BMV, CMV and AMV as examples, the moieties to be modified in the present invention for the purpose of inserting them into the plant genome are RNAs 1, 2 and 3 in FIG. 1. In the modified RNA3, the coat protein gene portion encoded in the 3' side is replaced by a desired exogenous gene.

Examples of the plants into which the virus genome is inserted are tobacco, soybean, cucumber, potato, rice plant, wheat, barley, corn, etc. but the plants are not limited only to them.

In the plant viruses described above, plants which become hosts of the respective viruses are different. For example, many plants belonging to Gramineae can be hosts of BMV. In inoculation of virus particles or virus RNA on tobacco plants, however, BMV does not multiply in plants. It is thus considered that tobacco cannot be a host of BMV. However, it is reported that when BMV particles or RNA is inoculated on tobacco protoplast, virus RNA is replicated in the cells and production of coat protein is induced (Maekawa et al. (1985) Ann. Phytopath. Soc. Japan, 51, 227–230). This suggests that if virus gene could be expressed in plant cells, it would be unnecessary to be bound to the conventional relationship between virus and host. According to the present invention, plants to which the present invention can apply can be chosen without being bound to the conventional concept of virus and host, even in the case of inserting virus gene into a genome of a plant cell. The plant cell as used herein refers to a concept including a protoplast.

(2) Construction of plant transformation vector

Virus RNA is extracted from virus particles by techniques known to extract RNA, for example, the guanidine method, the hot phenol method, sodium lauryl sulfate (SDS) phenol method, etc. In the case of BMV, CMV and AMV, the genome consists of several kinds of RNAs and the RNAs are fractionated and purified as RNAs 1, 2 and 3. Construction of the complementary DNA (cDNA) corresponding to each RNA can be made by utilizing conventional genetic manipulation technique (Ahlquist et al., (1984), J. Mol. Biol., 172: 369–383; Sambrook et al., (1989) Molecule Cloning, 2nd Edition, CSH Laboratory Press).

In the present invention, in the case of genomic RNA containing the replicase gene, for example, BMV, CMV and AMV, RNAs 1 and 2 are inserted into a genome of a plant cell, respectively, as a DNA molecule comprising i) a promoter which functions in a plant cell, ii) cDNA of RNA1 or 2 and iii) a terminator which functions in a plant cell. In the transformed plant cells in which such DNA molecule has been inserted, RNAs 1 and 2 are transcribed and 1a and 2a proteins are produced. The coat protein gene region of RNA3 cDNA is replaced with a desired exogenous gene to construct recombinant RNA3 cDNA. The recombinant is then inserted into the genome of a plant cell by which the 1a and 2a proteins described above are produced, as a DNA molecule comprising i) a promoter which functions in a plant cell, ii) recombinant RNA3 cDNA and iii) a terminator which functions in a plant cell. Alternatively, a recombinant RNA3 produced in vitro using the transcription vector is inoculated, on a plant cell by which the aforesaid 1a and 2a proteins are produced.

As the DNA molecule, there is used a DNA molecule comprising i) a promoter which functions in a plant cell, ii) cDNA of replicase gene of plant virus, for example, RNA1 or 2, or cDNA of recombinant virus genome, e.g., recombinant RNA3 cDNA and iii) a terminator which functions in a plant cell. As the transformation vector used to insert the DNA molecule into a genome of a plant cell, there are 2 kinds of vectors, for example, type (1) (pBICBR vector) and type (2) (pBICBMR vector) shown in FIG. 2. The two vectors possess the complete 1a or 2a translation region. In addition, type (1) vector bears cDNA of the full 5' and 3' non-translated regions of virus RNA; whereas type (2) vector bears cDNA of the full 5' non-translated region but is deleted of cDNA at the nucleotide portion corresponding to the 3' non-translated region. The 5' non-translated region of virus RNA is essential for translation efficiency and the synthesis of (+)-strand from (−)-strand, and the 3' non-translated region is essential for the synthesis of (−)-strand from (+)-strand. Therefore, the deletion of the 3' non-translated region results in deletion of the synthesis of (−)-strand from (+)-strand and thus loss in the multiplication efficiency of virus RNA but does not affect its translation efficiency. Where the full length CDNA of virus RNA is inserted into a genome of a plant cell using type (1) vector, the transcription product produced in the transformed cells multiplies as in wild type of virus RNA and also performs translation. On the other hand, where the 3' end-deleted cDNA of virus RNA is inserted into a genome of a plant cell using type (2) vector, the transcription product produced does not multiply in the transformed cells but translation is performed, whereby the translated product alone is produced. When virus RNA multiplies in large quantities, it is considered to cause disease in plants and adversely affect growth of the plants. In order to solve the problem, type (2) vector may thus be used.

As the promoter and terminator which function in a plant cell, there are cauliflower mosaic virus, (hereafter CaMV) 35S promoter and a terminator functional in a plant cell represented by CaMV terminator, etc. It has been revealed that BMV RNA variant having a nucleotide sequence of superfluous 7 nucleotides at the 5' end lacks infection efficiency (Janda et al., (1987) Virology, 158: 259–262). Therefore, in order to impart the translation efficiency to the nuclear transcription product of the full length cDNA of virus RNA inserted into a plant cell, it is necessary to accurately coincide the transcription initiation site of CDNA with the 5' end of virus RNA. In the case of using CaMV35S promoter, in order to introduce the full length cDNA of transcription initiation site right downstream the transcription initiation site, the recognition site of restriction enzyme (StuI, etc.) to cause the blunt end is introduced into the transcription initiation site of CaMV35S promoter by the site-directed mutagenesis and cDNA of virus RNA is introduced right downstream the transcription initiation site which is made the blunt end.

(3) Preparation of transformant by plant transformation vector

As the plant transformation method using *Agrobacterium tumefacien*, the leaf disk method (Horsch et al., (1985) Science, 227: 1229–1231) is most generally utilized. Ti plasmid has vir region and by the action of this region, T-DNA region in Ti plasmid can be inserted into a genome of a host cell of *A. tumefaciens* (Nester et al., (1984) Ann. Rev. Plant Physiol., 35: 387–413). As a gene introduction technique using Ti plasmid, the binary vector method has been widely used currently. According to this method, Ti plasmid is divided into a binary vector of T-DNA-deleted Ti plasmid having vir region and Ti plasmid containing T-DNA, and the binary vector is provided for use. The binary vector is a vector which can multiply both in *A. tumefaciens* and *E. coli*. DNA composed of the promoter, virus RNA cDNA and the terminator is incorporated into the T-DNA region in the binary vector to construct transformation vector. Such a transformation vector is introduced into *A. tumefaciens* cells carrying T-DNA-deleted Ti plasmid having vir region and said *A. tumefaciens* is inoculated on a host plant. By the action of vir region, the DNA-containing T-DNA region composed of said combination can be inserted into a genome of a host cell. The DNA having the aforesaid construction may also be inserted into a genome of a plant cell by other known gene introduction techniques, namely, electroporation to protoplast, liposome fusion, micro injection, particle gun to a plant tissue or the like.

For selection of the transformant, chemicals, such as kanamycin, hygromycin, phosphinothricin, etc. may be used. The transformant may be cultured in an appropriate medium to form callus, proliferation of the callus, if necessary and desired, subjected to adventive embryo differentiation or organ differentiation and then regenerated to a plant in a plant regeneration medium supplemented with a plant hormone.

Where the present invention is applied to a dicotyledonous plant, examples of the plant include Leguminosae (alfalfa, soybean, clover, etc.), Umbelliferae (carrot, celery, etc.), Cruciferae (cabbage, radish, rapeseed, etc.), Solanaceae (potato, tobacco, tomato, etc.). Where the present invention is applied to a monocotyledonous plant, the technique using *A. tumefaciens* cannot be utilized but it is possible to utilize electroporation to protoplast, liposome fusion, micro injection or particle gun to a plant tissue. Examples of the plants include Gramineae (rice plant, wheat, barley, corn, etc.).

To obtain the transformed cell having introduced cDNA of RNAs 1 and 2 inserted into the genome using type (1) or type (2) vector, (1) the transformed plant in which RNA1 cDNA has been inserted is hybridized with the transformed plant in which RNA2 cDNA has been inserted, and a plant which produces 1a and 2a proteins is selected. Alternatively, (2) the same plant is transformed by a vector incorporated with RNA1 cDNA and a vector incorporated with RNA2 cDNA, which have selection markers having different chemical resistances, (3) co-transformation is performed in the same cell using the electroporation method; and the like. Production of 1a and 2a proteins may be confirmed by inoculating RNA3 on the protoplast obtained from the transformed plant and the presence of coat protein by Western blotting. Further in order to obtain the pure line plant homologously having both cDNAs of RNA1 and RNA2 in a genome of a plant cell, the transformed plant which produces 1a and 2a proteins is subjected to anther culture, and the chromosome of haploid plant derived from pollen is doubled to obtain the pure line diploid. Then, by the technique described above, the transformed plant which produces 1a and 2a proteins may be selected.

(4) Construction of recombinant virus genomic RNA

In the present invention, DNA which encodes a desired polypeptide to be produced may also be recombined to a transcription vector for producing the transcription product in vitro and produced as RNA using the recombinant transcription vector.

In order to synthesize virus RNA in vitro, DNA-dependent RNA polymerase may be used. As DNA-dependent RNA polymerase, T7 RNA polymerase, SP6 RNA polymerase, *E. coli* RNA polymerase, etc. are commercially available. T7 RNA polymerase in which the nucleotide sequence in the promoter region and the transcription initiation site have been accurately revealed and has a high transcription efficiency (Dunn et al., (1983) J. Mol. Viol., 166: 477–535) may be advantageously used. The structure of 5' region of virus RNA has a very important role in replication of virus RNA, translation, etc. It is reported that when superfluous nucleotide sequence is added to the 5' end, the biological activity of virus RNA is drastically reduced (Janda et al., (1987) Virology, 158: 259–262). For this reason, in order to synthesize virus RNA having the same 5' nucleotide sequence as that of wild type in vitro, it is preferred that transcription be initiated accurately from the base of cDNA corresponding to the 5' end of virus RNA. Therefore, taking BMV as an example, the transcription initiation site is rendered the blunt end and, in order to introduce the full length cDNA of BMV RNA, the recognition site with restriction enzyme which causes the blunt end may be introduced at the transcription initiation site of T7 promoter. Thus, BMV RNA3 transcription vector pBTF3 is constructed (FIG. 3).

As a material for constructing the recombinant BMV RNA3 transcription vector, pBTF3 vector is utilized. pBTF3 vector is characterized by restriction enzyme map shown in FIG. 4. That is, pBTF3 vector is comprised of T7 promoter, BMV RNA3 cDNA and the gene of pUC vector which is vector for *E. coli*. A linker, etc. is ligated at the stuI site present in the coat protein gene portion of the vector described above to replace at the SacI site, SacI/SacI fragments (Nos. 1478–1782) are removed and self-ligation is performed to construct pBTF3 (Sac) vector.

Introduction of an exogenous DNA fragment into pBTF3 (Sac) is effected by introducing the exogenous DNA fragment having ATG translation initiation codon therein in the aforesaid vector at the HincII-SacI site. In order to introduce an exogenous gene into pBTF3 (Sac) vector at the HincII-SacI site, an exogenous gene DNA fragment having the blunt end capable of conjugating with HincII at the translation initiation codon site and having the SacI site at the terminator site may be ligated. That is, the exogenous DNA fragment having the modified ends as described above may be ligated with the ligation product of pBTF3(Sac) vector with HincII and SacI.

In production of the transcription product, recombinant pBTF3 vector is digested with EcoRI to form linear DNA.

Using this DNA as a template, re-combinant RNA3 is produced in large quantities by the in vitro transcription system involving ATP, UTP, CTP, GTP, cap analog (m$^7$GpppG) and T7 RNA polymerase.

(5) Expression of exogenous gene in transformant protoplast capable of producing replicase In a transformant having a replicase gene, for example, both cDNAs of RNAs 1 and 2 inserted into a genome, replicase having a biological activity, for example, 1a and 2a proteins are produced in all of the cells. That is, virus genome can be expressed in such a transformant by the mechanism of-transcription and translation of a plant. Furthermore, recombinant virus genomic RNA such as recombinant RNA3 cDNA, is inserted into a genome of a transformant having both cDNAs of RNAs 1 and 2 inserted in a genome, using transformation vector; recombinant RNA3 is transcribed by the transcription mechanism of a plant so that recombinant virus genomic RNA such as recombinant RNA3 is replicated by replicase e.g., 1a and 2a proteins produced in the plant cell, and at the same time, recombinant RNA4, which is a subgenome, is also synthesized in large quantities. Thus, the introduced exogenous gene and its product can be produced in large quantities (FIG. 9-2). Alternatively, by inoculating recombinant RNA3 on a transformed plant cell having introduced therein both cDNAs of RNAs 1 and 2 inserted at a genome, recombinant RNA3 can be replicated and recombinant RNA4 as its subgenome can be synthesized, in large quantities.

Existence of cDNA of the recombinant virus genomic RNA, e.g., RNA3, in the genome of a transformed plant can be confirmed by Southern blotting; production of recombinant RNA3 and recombinant RNA4 can be confirmed by Northern blotting; and production of the exogenous gene product can be confirmed by either the staining method or specrophotometric determination generally used that where, e.g., β-glucuronidase (GUS) gene is introduced, large quantities of GUS are produced in the infected cells.

Furthermore, the recombinant virus genomic RNA produced in vitro, for example, recombinant BMV RNA3 may also be inoculated on the protoplast prepared from the transformed plant. For the inoculation, there may be used known methods such as the polycation method, the polyethylene glycol method, the electroporation method, etc.

By inoculating recombinant RNA3 on such transformants, recombinant RNA4 is synthesized from recombinant RNA3 by the action of 1a and 2a proteins already produced in the transformants to produce the exogenous gene and its product in large quantities. Production of the exogenous gene product can be confirmed by the methods described above.

The process of the present invention enables efficient production of the gene product by inserting the virus replicase gene coded by the genome of RNA plant virus into a genome of a plant cell, producing the replicase by the mechanism of transcription and translation of the plant, and synthesizing mRNA of a desired gene in the plant cell in large quantities. Therefore, the present invention is extremely valuable from an industrial standpoint. According to the process of the present invention, the exogenous gene is incorporated into a plant transformation vector after the gene is wholly or partly recombined with the coat protein gene of virus genomic RNA, which is then transcribed as recombinant RNA in the plant cell or inoculated on a plant as recombinant RNA incorporated into the recombinant transcription vector and synthesized in vitro. Thus, the exogenous gene can be utilized extremely efficiently, as compared to the case where all virus genomic RNAs are synthesized in vitro followed by inoculating them on a plant. As the gene introduced into the recombinant virus genomic RNA, for example, recombinant RNA3, a variety of genes are considered. For example, genes of agriculturally useful protein, functional protein, protein used as a drug, e.g., interferon, etc. may be introduced. Further where the process is applied to breeding of crops, expression of a character can be acquired with a higher frequency, since the amount of mRNA produced by the exogenous gene is larger than the conventional process in which several copies of the exogenous gene are inserted into a genome of a plant cell. Where the exogenous gene is, e.g., the coat protein gene of a virus, the process is applicable to breeding of a virus-resistant plant; when the exogenous gene is cowpea trypsin inhibitor gene, the process is applicable to breeding of a insert-resistant plant having a wide spectrum. Furthermore, where antisense RNA complementary to endogenous RNA is inserted and antisense RNA is synthesized in a plant cell in large quantities, translation of endogenous RNA can be prevented; in this case, it is possible to regulate expression of a plant gene.

EXAMPLES

Hereafter the present invention is described more specifically with reference to the examples but is not deemed to be limited thereto.

Example 1
Construction of BMV RNA transcription vector and plant transformation vector A. Preparation of cDNA of BMV RNAs 1, 2 and 3

As BMV, ATCC66 strain was used. For multiplication of virus, barley (*Hordeum vulagare* L., species: GOSE-SHIKOKU) was used and virus particles were purified by known fractional centrifugation (Okuno et al., (1978) J. Gen. Viol., 38: 409–418). Using purified BMV, phenol extraction was repeated 3 to 4 times in the presence of bentonite and SDS. Then, ethyl ether treatment and ethanol precipitation were performed to give RNA.

The resulting RNA solution was subjected to a standard separation method using low melting point agarose electrophoresis (Shambrook et al., (1989) Molecular Cloning, 2nd, CSH Laboratory) to give RNAs 1, 2 and 3, respectively. From each of the resulting RNAs, the full length cDNAs of RNAs 1, 2 and 3 were prepared by the known method (Ahlquist et al., (1984), J. Mol. Biol., 172: 369–383) and cloned to pUC vector, to produce the named pBB1, 2 and 3, respectively. Plasmids pBB1, 2 and 3 have the SnaBI site at the site corresponding to the 5' end of the full length BMV RNA and have the EcoRI site just downstream the 3' end.

B. Construction of BMV RNA transcription vector and synthesis of infectious RNA in vitro B-1. Construction of BMV RNA transcription vector (pBTF1, 2 and 3)

In order to synthesize BMV RNA in vitro, DNA-dependent RNA polymerase is indispensably required. As the DNA-dependent RNA polymerase, T7 RNA polymerase, SP6 RNA polymerase and *E. coli* RNA polymerase, etc. are commercially available. In this example, the in vitro BMV RNA synthesis system using T7 RNA polymerase, in which the nucleotide sequence in the promoter region and the transcription initiation site have been revealed and has a high transcription efficiency (Dunn et al., (1983) J. Mol. Viol., 166: 477–535), was used. The 5' end structure of nucleic acid in virus RNA at the 5' end has an extremely important function in replication of virus RNA or translation, etc. It is reported that when superfluous nucleotide sequence is added to the 5' end, the biological activity of virus RNA is drastically reduced (Janda et al., (1987) virology, 158: 259–262). For this reason, in order to synthesize virus RNA having the same nucleotide sequence at the 5' end as that of wild type in vitro, transcription should be initiated precisely from the site in cDNA corresponding to the 5' end of BMV RNA. Accordingly, in order to add the blunt end at the transcription initiation site and introduce the full length cDNA of BMV RNA, the inventors attempted to introduce a restriction enzyme recognition site at the transcription initiation site of T7 promoter.

B-1-1. Synthesis of T7 promoter

Using a DNA synthesizer (Applied Biosystems Co., Ltd., Model 381A), two oligonucleotides composed of 31 nucleotides (see SEQ ID NOS: 1 and 2)

d(CTAGATGCATATAGTGAGTCGTATTAATTTA)

and d(AGCTTAAATTAATACGACTCACTATATGCAT)

were synthesized. After completion of the synthesis, the oligonucleotides were purified by high performance liquid chromatography in a conventional manner. After the recovered oligonucleotide solution was neutralized by adding 1/200 volume of 2N HCl, the mixture was added to NENSORB 20 (manufactured by Du Pont Co., Ltd.) to perform desalting. Firstly, its column was equilibrated with 2 ml of methanol (for high performance liquid chromatography, manufactured by Nakarai Tesque Co., Ltd.), 2 ml of solution A (0.1M Tris-HCl, 10 ml tri-ethylamine (TEA), 1 mM $Na_2$-EDTA, pH 7.7). Next, TEA was added to the sample in a proportion of 1.4 μg/ml and the resulting mixture was flown through the column to cause adsorption. After the column was washed with 6–9 ml of solution A and 3 ml of ion exchange water, the oligonucleotide was eluted with 400 μl of 50% ethanol (special grade, manufactured by Nakarai Tesque Co., Ltd.). The eluted oligonucleotide solution was evaporated to dryness under reduced pressure using an evaporator. The residue was dissolved in ion exchange water to prepare 1 μg/ml of oligonucleotide solution.

The 5' and 3' ends of these synthetic oligonucleotides were phosphorylated. That is, a reaction solution containing 1 μl of each oligonucleotide (1 μg/ ml), 20 μl of 10 mM ATP, 20 μl of 10× kinase solution (500 mM Tris-HCl, pH 7.5, 100 mM $MgCl_2$, 100 mM dithiothreitol (DTT)), 4 μl of T4 polynucleotide kinase (4 units/μl, manufactured by Takara Shuzo Co., Ltd.) and 155 μl of ion exchange water was reacted at 37° C. for an hour to effect phosphorylation of the oligonucleotides. After the reaction, the enzyme was inactivated by a heat treatment at 65° C. for 10 minutes. The reaction solution was treated twice with phenol, once with phenol/chloroform, once with chloroform and 3 times with ethyl ether. Thereafter the reaction solution was allowed to stand for 30 to 40 minutes under reduced pressure and ethyl ether present in the reaction solution was completely removed. The reaction solution was added to NENSORB 20 column and the phosphorylated oligonucleotides were purified as described above. Thereafter the solution was evaporated to dryness and the residue was dissolved in distilled water in a concentration of 50 ng/ml. The solution was then provided for the following operation.

These synthetic oligonucleotides were annealed to synthesize T7 promoter. The sequence of this promoter has HindIII site at the 5' end and XbaI site as being staggered, in addition to the consensus sequence of T7 promoter, and further has NsiI site at the (+4) position from the transcription initiation site.

B-1-2. Introduction of the full length cDNA of BMV RNA into transcription vector pUCT The synthesized T7 promoter was introduced into pUC19 at the HindIII/XbaI site to construct transcription vector pUCT (FIG. 3). pUCT was treated with NsiI and T4 DNA polymerase thereby to remove the nucleotides of T7 promoter up to the (+1) position and form the blunt end at the (−1) position. The SnaBI/EcoRI fragment containing the full length cDNAs of respective BMV RNAs of pBB1, pBB2 and pBB3 was ligated with a large fragment of pUCT which had been treated with NsiI and T4 polymerase followed by treatment with EcoRI to construct transcription vectors pBTF1, pBTF2 and pBTF3 of BMV RNAs 1, 2 and 3, respectively.

B-2. Synthesis of infectious RNA in vitro

The respective DNAs of transcription vectors pBTF1, 2 and 3, in which the respective full length cDNAs of RNAs 1, 2 and 3 have been introduced right downstream the transcription initiation site of T7 promoter and the EcoRI site is present right downstream the full length cDNA, were purified by the cesium chloride centrifugation method (Sambrook et al., (1989) Molecular Cloning, 2nd, CSH Laboratory). After 3 μg of each of the purified DNAs was cleaved with EcoRI, treatment with phenol/chloroform was performed followed by ethanol precipitation using 20 μg of tRNA as a carrier. After 16.8 μl of distilled water, 10 μl of 5× transcription buffer (200 mM Tris-HCl (pH 7.5), 30 mM $MgCl_2$, 10 mM spermidine, 50 mM NaCl), 5 μl of 100 mM DTT, 1.8 μl of DNase/RNase free bovine serum albumin (2.8 mg/ml), 2.5 μl of RNasin (40 units/ml), 2.5 μl of 10 mM ATP, 2.5 μl of 10 mM UTP, 2.5 μl of 10 mM CTP, 0.4 μl of 10 mM GTP and 5 μl of 5 mM cap analog ($m^7$GpppG) were added to the resulting precipitates, the mixture was gently mixed. Then 1 μl of T7 polymerase was added and the mixture was reacted at 37° C. for an hour. Thereafter, 1.3 μl of DNase (1 unit/ml) was added and the mixture was reacted at 37° C. for an hour to decompose template DNA. The reaction solution was treated once each with phenol/chloroform and with chloroform followed by ethanol precipitation using 20 μg of tRNA as a carrier. The precipitates were suspended in 10 μl of distilled water.

The respective transcription products of cDNAs of BMV RNAs 1, 2 and 3 synthesized in vitro by the process described above were mixed with each other and an equal volume of 2× inoculation buffer (100 mM Trisphosphate (pH 8.0), 500 mM NaCl, 10 mM EDTA, 1% (W/V) bentonite) was added to the mixture. The thus obtained solution was used as an inoculation solution. Carborundum (600 mesh) was sprinkled over barley leaf, which was a systemic infection host, and 5 to 10 μl of inoculation solution drops were speared and inoculated on the leaf. Immediately after inoculation, carborundum on the leaf was washed off with tap water. For about 2 weeks, the barley leaf was grown in a growth chamber (8,000 LUX) at 25° C., where the leaf expressed systemic symptoms. It was thus confirmed that the transcription products of transcription vectors pBTF1, 2 and 3 were infectious.

C. Construction of plant transformation vector

C-1. Introduction of the restriction enzyme recognition site into CaMV35S promoter at the transcription initiation site It was attempted to introduce the full length cDNA of BMV RNA between the promoter and terminator recognized by a DNA-dependent RNA polymerase present in a plant cell. As the promoter, CaMV35S promoter was used, taken into account that its transcription amount was large and the transcription initiation site and the nucleotide sequence in the promoter region were revealed. Furthermore, it has been revealed that BMV RNA mutant having the nucleotide sequence of superfluous 7 bases at the 5' end has no infectious ability (Janda et al., (1987) Virology, 158: 259–262). Therefore, in order to impart the ability of multiplication to the nuclear transcription product of the full length cDNA of BMV RNA inserted in a plant cell, it is necessary to accurately coincide the transcription initiation site of cDNA with the site in cDNA corresponding to the 5' end of BMV RNA. Thus, for the purpose of introducing the full length cDNA of BMV RNA right downstream the transcription initiation site, the recognition site of restriction enzyme was introduced into CaMV35S promoter at the transcription initiation site by the site-directed mutagenesis.

C-2. Site-directed mutagenesis (FIG. 5)

Plasmid pCAM35 has CaMV35S promoter region (7016–7434) of CaMV CM1841 strain immediately upstream pUC18-derived polylinker sequence and 35S terminator region of CaMV CM1841 strain. In order to prepare single-stranded DNA in the CaMV35S promoter region, the PstI/EcoRI fragment of pCAM35 was introduced into pUC18 at the PstI/EcoRI site to construct pCAM35EP. *E. coli* MV1184 strain was transformed by pCAM35EP and single stranded DNA was prepared utilizing helper phage M13K07.

In order to introduce the StuI site into the transcription initiation siLe, the oligonucleotide of 25 bases (see SEQ ID NOS: 3):

d(GTAGGCCTCTCCAAATGAAATGAAC)

complementary to the transcription initiation site of the prepared single-stranded DNA, except for 3 mismatches, was synthesized and prepared by the procedure described in B-1-1. In an Eppendorf tube for 1.5 ml were charged 1 μl of single-stranded DNA (20 μg/μl), 1 μl of synthetic oligonucleotide (2 μg/μl), 20 μl of 10× annealing buffer (200 mM Tris-HCl (pH 7.5), 100 mM MgCl$_2$, 500 mM NaCl, 10 mM DTT) and 178 μl of distilled water. After treating at 62° C. for 15 minutes, the mixture was slowly cooled at room temperature for 7 minutes to anneal the synthetic oligonucleotide to single-stranded DNA. After the annealing, 40 μl of Klenow buffer (100 mM Tris-HCl (pH 7.5), 50 mM MgCl$_2$, 50 mM DTT), 20 pl of dNTP solution (2 mM each of dATP, dCTP, dGTP and dTTP), 10 μl of Klenow fragment (4 units/ml) and 130 μl of distilled water were added, the mixture was subjected to enzyme reaction at 22° C. for 5 hours to synthesize complementary DNA strand using the synthetic oligonucleotide as a primer. After the reaction, the reaction solution was treated with phenol, with phenol/chloroform and with ethyl ether and then precipitated with ethanol to give double-stranded DNA precipitates. After this double-stranded DNA was cleaved with PvuII, the cleavage product was treated with phenol/chloroform and then precipitated with ethanol. With the resulting precipitates were mixed 1.5 μl of loading buffer (0.89M Tris-borate, 2 mM EDTA, 0.2% (W/V) bromophenol blue, 0.2% (W/V) xylene cyanol) and 432 μl of formaldehyde. After the treatment at 95° C. for 5 minutes, the mixture was quenched with ice water. This sample was loaded on 3.5% polyacrylamide-7M urea gel (15 cm×15 cm, thickness of 2 mm, slot width of 1 cm), which was subjected to electrophoresis at 200 V for 2 hours. Thus, single-stranded DNA synthesized by the primer was isolated. After staining with ethydium bromide (0.5 μg/ml), the gel was washed 3 times with about 30 ml of ion exchange water to remove an excess of ethydium bromide and urea. By exposure to UV, the desired band was excised and the gel was passed through 1 ml of syringe (Terumo Co., Ltd.) to make into pieces. The pieces of the gel were added to 7 ml of elution buffer (500 mM ammonium acetate, 10 mM magnesium acetate, 1 mM EDTA, 0.1% SDS). The mixture was allowed to stand at 37° C. overnight. After centrifugation at 5000×g for 3 minutes, the supernatant was treated twice with phenol, once with phenol/chloroform, once with chloroform and 3 times with ethyl ether. After the solution was concentrated to 4-fold with 2-butanol, a 2-fold volume of ethanol and 10 μl of tRNA (2 mg/ml) was added to the concentrate. By ethanol precipitation, single stranded DNA precipitates were obtained and the precipitates were dissolved in 30 μl of distilled water. By mixing 5 μl of the recovered single-stranded DNA (0.2 μg/μl), 1.5 μl of M13 reverse primer (50 ng/μl, M13 primer RV, manufactured by Takara Shuzo Co., Ltd.), 1 μl of annealing buffer (100 mM Tris-HCl (pH 7.5), 100 mM MgCl$_2$, 500 mM NaCl), 1.5 μl of TE buffer (10 mM Tris-HCl (pH 8.0), 1 mM EDTA) and 1 μl of Klenow fragment (4 units/μl), double-stranded DNA fragment was synthesized and the StuI site was introduced at the transcription initiation site. The synthesized fragment of 35S promoter region was cleaved with EcoRI and the cleavage product was introduced into pUC18 at the EcoRI/SmaI site to construct pCAP35 containing the modified 35S promoter region. By cleaving pCaP35 with stuI, the transcription initiation site can be rendered the blunt end and the full length cDNA of BMV RNA can be introduced right downstream the transcription initiation site.

C-3. Construction of plant transformation vector (pBICBR series) (FIG. 6)

By inserting the full length cDNA of BMV RNA in a genome of a plant, a vector was constructed to create a transformed plant in which the transcription product has the ability of translation and multiplication as in wild type virus RNA.

CaMV35S promoter, pUC18-derived polylinker site and CaMV terminator were introduced into Agrobacterium binary vector pBIN19 (Bevan et al., (1984) Nucl. Acids Res., 12: 8711–8721) for plant transformation at the EcoRI/HindIII site. The resulting plasmid is pBIC35. After pBIC35 was cleaved with EcoRI, the digestion product was rendered blunt end by T4 DNA polymerase treatment and SalI linker was added. After cleaving with SalI, self ligation was performed to construct pBICT(-E) deleted of CaMV35S promoter. Then, after further adding EcoRI linker, pBICT (-E) cleaved with SmaI was subjected to self ligation to construct pBICTE having the EcoRI site modified from the SmaI site. On the other hand, pCaP35 containing CaMV35S promoter modified by introducing the StuI site into CaMV35S promoter at the transcription initiation site by the site-directed mutagenesis was cleaved with EcoRI. Then, both ends were rendered blunt ends by T4 DNA polymerase treatment and SalI linker was added to the both ends. By cleaving with SalI and BamHI, DNA fragment containing the modified CaMV35S promoter was obtained. The fragment was introduced into pBICTE at the SalI/BamHI site to construct pBICP35.

Next, the SnaBI/EcoRI fragments of pBB1, pBB2 and pBB3 containing the full length cDNA fragment of BMV RNAs 1, 2 and 3 were introduced into pBICP35 at the stuI/EcoRI site, respectively to construct plant transformation vectors pBICBR1, 2 and 3, respectively (FIG. 6).

C-4. Construction of plant transformation vector (pBICBMR series) (FIG. 7-1-3)

By introducing the cDNA, in which the portion corresponding to 3' end of BMV RNA was deleted in a genome of a plant cell, a vector was constructed to create a transformant in which the transcription product synthesized has the ability of translation but does not have the ability of multiplication as in wild type virus RNA.

After pBB1 containing the full length cDNA of BMV RNA1 was cleaved with XhoI, the cleavage product was treated with T4 DNA polymerase to render both ends blunt. Then, EcoRI linker was added thereto. After further cleaving with EcoRI, self ligation was performed. As the result, pBB1(-3) having deletion of about 200 bases downstream XhoI in the cDNA corresponding to the 3' non-translated region of RNA1 was obtained. The SnaBI/EcoRI fragment containing RNA1 cDNA of pBB1(-3) was introduced into pBICP35 at the StuI/EcoRI site to construct plant transformation vector pBICBMR1 (FIG. 7-1).

After pBB2 containing the full length cDNA of BMV RNA2 was cleaved with PstI and HindIII, the cDNA fragment was introduced into pUC18 at the PstI/HindIII site to obtain pBB2(−H) containing cDNA deleted of the 3' non-translated region of RNA2. After pBB2(−H) was cleaved with HindIII, the cleavage product was treated with T4 DNA polymerase to render both ends blunt. Then, EcoRI linker was added thereto. After further cleaving with EcoRI, self ligation was performed. As the result, pBB2(−3) having deletion of about 200 bases downstream HindIII in the cDNA corresponding to the 3' non-translated region of RNA2 was obtained. The SnaBI/EcoRI fragment containing RNA2 cDNA of pBB2(−3) was introduced into pBICP35 at the stuI/EcoRI site to construct plant transformation vector pBICBMR2 (FIG. 7-2).

After pBB3 containing the full length cDNA of BMV RNA3 was cleaved with PstI and HindIII, the cDNA fragment was introduced into pUC18 at the PstI/HindIII site to obtain pBB3(−H) containing cDNA deleted of the 3' non-translated region of RNA3. After pBB3(−H) was cleaved with HindIII, the cleavage product was treated with T4 DNA polymerase to render both ends blunt. Then, EcoRI linker was added thereto. After further cleaving with EcoRI, self ligation was performed. As the result, pBB3(−3) having deletion of about 200 bases downstream HindIII in the cDNA corresponding to the 3' non-translated region of RNA3 was obtained. The SnaBI/EcoRI fragment containing RNA3 cDNA of pBB3(−3) was introduced into pBICP35 at the StuI/EcoRI site to construct plant transformation vector pBICBMR3 (FIG. 7-3).

Example 2

Expression of the respective BMV genes in transformed plant cell

A. Introduction of plant transformation vector into *A. tumefaciens*

On one NB agar medium (0.8% Nutrient Broth, 1.5% Bacto Agar), *E. coli* DH5α strain (harboring pBICBR or pBICBMR vector), *E. coli* HB101 strain (harboring helper plasmid pRK2013) and *A. tumefaciens* LBA4404 strain (harboring Ti plasmid deleted to T-DNA region) were inoculated, respectively followed by incubation at 30° C. for 2 days. After the incubation, 3 kinds of bacteria were mixed with a sterilized platinum loop followed by incubation at 30° C. for further 2 days. The mix-cultured bacteria was streaked on AB agar medium (Table 1) containing 50 μg/ml of kanamycin and cultured at 30° C. for 2 days to obtain a single colony. This colony is *A. tumefaciens* LBA4404 strain harboring transformation vector.

TABLE 1

| AB medium | | |
|---|---|---|
| Solution 1 | $K_2HPO_4$ | 12 g |
| | $NaH_2PO_4$ | 4 g |

TABLE 1-continued

| AB medium | | |
|---|---|---|
| Solution 2 | $NH_4Cl$ | 4 g |
| | $MgSO_4.7H_2O$ | 1.2 g |
| | KCl | 0.6 g |
| | $CaCl_2$ | 0.6 g |
| | $FeSO_4.7H_2O$ | 10 mg |
| Solution 3 | Glucose | 20 g |

B. Inoculation of *A. tumefaciens* on tobacco and selection of transformants

As tobacco for inoculation (*Nicotiana tabacum* cv. Petit Habana SR1), a sterile plant derived from a sterilized seed was used. About 100 μl of tobacco seed in an Eppendorf's tube of 1.5 ml was washed with 1 ml of 70% ethanol. Next, 1.5 ml of 20% antiformin was added to the tobacco seed. While stirring for a second every other 4 minutes, the mixture was allowed to stand at room temperature for 20 minutes to sterilize the seed. After the sterilization, the seed was washed 3–4 times with sterile water and inoculated on LS1 medium (Table 2) in a plastic Petri dish (Seibu Co., Ltd., 90 mm in diameter, 20 mm in depth) followed by growing at 26° C. under 8,000 LUX. The young plant grown to about 1 cm was transplanted to a biopot (Nippon Medical Chemical Machine Co., Ltd.) with LS8 medium (Table 2). The plant grown to about 10 cm tall was used for

*A. tumefaciens* inoculation.

*A. tumefaciens* harboring transformation vector was cultured by shaking (120 rpm) at 30° C. for 2 days in AB liquid medium containing 50 μg/ml of kanamycin. Operations subsequent thereto were all performed aseptically. The tobacco leaf grown aseptically was cut into 1 cm×1 cm and immersed in the aforesaid culture broth of *A. tumefaciens* for a minute. This leaf piece was put on a paper towel, which had been previously sterilized, to remove an excess of the bacterial solution. The leaf piece was put on LS1 medium (Table 2), turning the back surface up. After incubation at 26° C. for 48 to 72 hours, the leaf piece was transferred onto LS1 liquid medium containing 500 μg/ml of carbenicillin and cultured at 26° C. for 2 days under 700 LUX to fully remove *A. tumefaciens*. After the incubation, this leaf piece was put on a paper towel, which had been previously sterilized, to remove LS1 liquid medium. Then the leaf piece was transferred onto LS4 medium (Table 2) containing 150 μg/ml of kanamycin and 100 μg/ml of carbenicillin, and cultured at 26° C. for about 2 to 3 weeks under 8,000 LUX. A sprouted shoot of 5–10 mm tall was cut out of callus with a sterilized surgical knife and transferred onto MSR medium containing 100 μg/ml of kanamycin and 150 μg/ml of carbenicillin (LS plate medium containing 525 μg/ml of naphthaleneacetic acid and 100 μg/ml of 6-benzyladenine, using Gelangum instead of agar). Two weeks after, the young plant grown to about 5 cm in the whole body was transplanted to a flowerpot having a diameter of 12 cm and the plant was covered with a transparent plastic box for conditioning the plant for several days. Then, the plant was grown in a growth chamber.

Kanamycin-resistant transformed tobacco by transformation vectors pBICBR1, pBICBR2 and pBICBR3 were named BR1, BR2 and BR3, respectively, and kanamycin-resistant transformed tobacco by transformation vectors pBICBMR1, pBICBMR2 and pBICBMR3 were named BMR1, BMR2 and BMR3, respectively. Furthermore, transformed tobacco by transformation vector pBIC3GUS(Hc) was named BR3GUS(Hc).

TABLE 2

LS medium
Preparation method for LS medium stock solution
(per 200 ml)

| Stock | | |
|---|---|---|
| Stock 1 | NH$_4$NO$_3$ | 33 g |
| | KNO$_3$ | 38 g |
| Stock 2 | MgSO$_4$.7H$_2$O | 7.4 g |
| | KH$_2$PO$_4$ | 3.4 g |
| Stock 3 | CaCl$_2$.2H$_2$O | 8.8 g |
| Stock 4 | Na$_2$-EDTA | 0.746 g |
| | FeSO$_4$.7H$_2$O | 0.666 g |
| Stock 5 | H$_3$BO$_3$ | 0.124 g |
| | MnSO$_4$.4H$_2$O | 0.172 g |
| | ZnSO$_4$.4H$_2$O | 0.446 g |
| | KI | 0.017 g |
| | Na$_2$MoO$_4$.2H$_2$O | 0.005 g |
| Stock 5' | CuSO$_4$.5H$_2$O | 0.05 g |
| | CoCl$_2$.6H$_2$O | 0.05 g |
| Stock 6 | Thiamine-HCl | 0.008 g |
| | Myo-Inositol | 2.0 g |
| Stock 7 | Naphthalene acetic acid (NAA) | 0.042 g |
| Stock 8 | 6-Benzyladenina (BAP) | 0.004 g |
| Stock 9 | 6-Benzyladenina (BAP) | 0.1 g |
| Stock 10 | Myo-Inositol | 2 g |
| | Glysin | 0.04 g |
| | Pridoxln-HCl | 0.01 g |
| | Nicotinic acid | 0.01 g |
| | Thiamine-HCl | 0.02 g |

*BAP first is dissolved (boil in hot water), then add water to be 200 ml.

Preparation method for LS medium (1 l)

| | |
|---|---|
| 1 | add 2 ml of Stock 5' to 200 ml of new Stock 5, and use the resultant solution thereafter. |
| 2 | add each 10 ml of Stocks 1, 2, 3, 4, 5 and 6, respectively. |
| 3 | add Hormone Stock according to the following table. |
| 4 | add 30 g of sucrose to be 1 l by ion-exchanged water. |
| 5 | adjust its pH to 5.8–6.2 using NaOH or KOH. |
| 6 | add 0.8–1% of agar, and autoclave-sterilize using a pot incubator. |
| 7 | after cooling the pot to 50–60° C., shake and mix it gently, and stand at room temperature to solidify. In case antibiotic is added, after cooling the pot to 50–60° C., filter-sterilized antibiotic is added. |

Hormone concentration (in case of tabacco) (per 1 l)

| | Stock 7 | Stock 8 | Stock 9 |
|---|---|---|---|
| for callus (LS1) | 10 ml | 10 ml | — |
| for germination (LS4) | 0.5 ml | — | 10 ml |
| for rooting (LS7) | 2.5 ml | 5 ml | — |
| for young plant (LS8) | — | — | — |

C. Analysis on expression of each gene of BMV inserted into tobacco genome

For examining that each gene of BMV inserted is expressed in the transformed plant showing kanamycin resistance, analysis on expression of the introduced 1a gene was made by inoculating a mixture of RNAs 2 and 3 on the protoplast prepared from the transformed tobacco BR1 or BMR1, and analysis on expression of 2a gene was made by inoculating a mixture of RNAs 1 and 3 on the protoplast prepared from the transformed tobacco BR2 or BMR2. RNAs 1, 2 and 3 were synthesized in vitro from pBTF1, 2 and 3 by the process described in Example 1B.

In the cell in which virus replicase, 1a and 2a proteins, are expressed, it is considered that RNA4, which is mRNA of coat protein, would be synthesized from the inoculated RNA3 and coat protein of BMV would be accumulated in the cell. It is considered that coat protein would not be directly translated from RNA3 but would be translated by replicase via RNA4 synthesized from (−)-stranded RNA3 (Miller et al., (1985) Nature, 313: 68–70); by detecting the production of coat protein, production of replicase, or 1a and 2a proteins which are subunits of the enzyme can be indirectly detected. Thus, analysis on production of coat protein was made by Western blotting using anti-BMV antibody.

C-1. Preparation of protoplast

For preparation of protoplast, the 4th to 5th leaf of tobacco plant at 15–20 cm in leaf length stage were used. The back epidermis of the cut tobacco leaf was peeled apart and immersed in 0.5M mannitol solution (its pH was adjusted to 5.6–5.8 with KOH) containing 1% Cellulase Onozuka R-10 (Kinki Yakult Co., Ltd.) and 0.05% macrozyme R-10 (Kinki Yakult Co., Ltd.), in a flask of 100 ml volume. While the flask was gently shaken every other 15 minutes, the leaf was treated at 26° C. for 2 hours. The undecomposed tissue contained in the resulting protoplast suspension was filtered through a 4- to 6-layered gauze and transferred to a. glass-made centrifuging tube for 50 ml. The protoplast was collected by centrifugation at 100×g for 2 minutes. Centrifugal washing was repeated twice further with 0.5M mannitol solution.

C-2. Inoculation of BMV RNA on tobacco protoplast

A suspension of protoplast in 0.5M mannitol was transferred to 4 to 6 polypropylene made culture tubes of 10 ml each volume (Nissui Pharmaceutical Co., Ltd., #06480). The protoplast was collected by centrifugation at 100×g for 2 minutes and the supernatant was removed. To the protoplast was added 0.7 ml of T solution (0.5M mannitol, 40 mM CaCl$_2$) containing 2–10 μg of BMV RNA and 10 μg of tRNA. After thoroughly mixing them, 0.7 ml of PEG solution (40% PEG 4000, 0.5M mannitol, 40 mM CaCl$_2$) was immediately added to the mixture. Each tube was turned upside down to gently mix and shaken on ice for 30 minutes at a low speed. Thereafter, about 8 ml of T solution was added to the mixture. Each tube was turned upside down to gently mix and settled on ice for 30 minutes. After the protoplast was collected by centrifugation at 100×g for 2 minutes, centrifugal washing was repeated 3 times with High-pH High-Ca$^{2+}$buffer (0.7M mannitol, 50 mM CaCl$_2$, 50 mM glycine, pH 8.5) to remove PEG and non-adsorbed RNA. The protoplast was suspended in 3 ml of 0.7 i medium (0.2 mM KH$_2$PO$_4$, 1 mM KNO$_3$, 1 mM MgSO$_4$.7H$_2$O, 10 mM CaCl$_2$.2H$_2$O, 0.1 μM KI, 0.01 μM CuSO$_4$.5H$_2$O, 0.7M mannitol, 2500 units/ml micostatin, 200 μg/ml chloramphenicol, pH 6.5) followed by incubation at 26° C. for 48 hours.

C-3. Preparation of antibody and Western blotting analysis

Anti-BMV sera were purified by the ammonium sulfate method to obtain γ-globulin fraction. Acetone powder was prepared from the tobacco protoplast, and reacted with the purified anti-BMV antibody described above, whereby the antibody non-specifically binding to the plant component was removed. After the protein extracted from the protoplast inoculated with BMV RNA was subjected to SDS-polyacrylamide gel electrophoresis, the isolated protein was electrically transferred onto a membrane (Immobilon-P, manufactured by Millipore Co., Ltd.) by the method of Towbin et al. (Towbin et al., (1979) Proc. Natl. Acad. Sci. USA, 76: 4350–4354). After the transfer, detection of BMV coat protein was made by coloring reaction on NBT-BCIP as substrate, using the purified anti-BMV antibody diluted to 1/400 as a primary antibody and anti-rabbit IgG-goat IgG labeled with alkaline phosphatase as a secondary anti-body.

C-4. Analysis of the introduced gene product in BR1 and 2 plant cells

RNA 2+3 synthesized in vitro was inoculated on the protoplast prepared from a BR1 plant. Further as positive control, RNA 1+2+3 was inoculated on the protoplast. Forty eight hours after the inoculation, relative evaluation of coat protein synthesized in the transformed plant was made by Western blotting analysis. The evaluation was made as follows, when an average value on the expression degree of coat protein gene in positive control was made 100%.
Average value for expression of coat protein:

| BR1 plant inoculated with RNA 1 + 2 + 3 | 100 |
| BR1 plant inoculated with Mock | 0 |
| BR1 plant inoculated with RNA 1 + 3 | 0 |
| BR1 plant inoculated with RNA 2 + 3 | 110 |

In the BR1 plant inoculated with RNA 2+3, coat protein was detected on a level similar to that in the BR1 plant inoculated with RNA 1+2+3. It was thus considered that complete 1a protein was produced in all cells of BR1 plant.

Also in the case where RNA 1+3 was inoculated on the protoplast prepared from BR2 plant, coat protein was detected as follows.
Average value for expression of coat protein:

| BR2 plant inoculated with RNA 1 + 2 + 3 | 100 |
| BR2 plant inoculated with Mock | 0 |
| BR2 plant inoculated with RNA 2 + 3 | 0 |
| BR2 plant inoculated with RNA 1 + 3 | 98 |

In the case where RNA 1+3 was inoculated without inoculating RNA 1+2+3, coat protein was produced in the protoplast on a level similar to that of the group inoculated with RNA 1+2+3. It was thus considered that complete 2a protein was produced in all cells of BR2 plant.

C-5. Analysis of the introduced gene product in BMR1 and 2 plant cells

RNA synthesized in vitro was inoculated on the protoplast prepared from BMR1 and 2. Forty eight hours after the inoculation, coat protein in the protoplast was detected by western blotting. The results reveal that also where RNA 2+3 was inoculated on the protoplast prepared from BMR1, in which cDNA of RNA1 using pBICBMR vector having deletion only at the 3' non-translated region, coat protein was detected on a level similar to that in the case inoculated with RNA 1+2+3. Also where RNA 1+3 was inoculated on BMR2, coat protein was detected. The evaluation was made as follows, when an average value on the expression degree of coat protein gene in positive control was made 100%.
Average value for expression of coat protein:

| BMR1 plant inoculated with RNA 1 + 2 + 3 | 100 |
| BMR1 plant inoculated with Mock | 0 |
| BMR1 plant inoculated with RNA 2 + 3 | 105 |
| BMR1 plant inoculated with RNA 1 + 3 | 0 |
| BMR2 plant inoculated with RNA 1 + 2 + 3 | 100 |
| BMR2 plant inoculated with Mock | 0 |
| BMR2 plant inoculated with RNA 2 + 3 | 0 |
| BRM2 plant inoculated with RNA 1 + 3 | 90 |

In BMR1 or BMR2, it is shown that all 1a proteins or 2a proteins necessary for replication of virus may be relied on transcription and translation from the plant genome, since the transcription product of cDNA of RNA1 or RNA2 introduced in the genome of plant lacks the ability of replication. It has also be revealed that each gene of virus could be made independent from the complicated control mechanism of virus but dependent on the mechanism of transcription and translation of the plant.

Example 3

Production of the exogenous gene product in transformed tobacco protoplast

A. Construction of recombinant RNA3 transcription vector pBTGUS (FIG. 4)

After BMV RNA3 transcription vector pBTF3 was cleaved with StuI, SacI linker was added to the blunt end to modify the StuI site into the SacI site, cleavage with SacI and self ligation were performed to construct pBTF3(Sac) deleted of the SacI/StuI fragment (Nos. 1478–1782) of pBTF3.

Then, it was attempted to construct transcription vector recombined with an exogenous gene between the HincII site and SacI site cleaved by 6 base pairs from the ATG translation initiation site of pBTF3(Sac) coat protein gene.

As a reporter gene for gene expression using BMV, GUS gene was used. HindIII/EcoRI fragment carrying GUS gene, from which promoter of pBI101 (Toyobo Co., Ltd., K1050) had been removed, namely, a fragment containing GUS gene, polylinker sequence and nopaline synthase (NOS) terminator was introduced into pUCL8 at the HindIII/EcoRI site to construct pUCBI101. It was attempted to excise GUS gene fragment having 7 kinds of 5' ends from pUCBI101. After cleaving with the respective restriction enzymes of HindIII, SphI, PstI, BamHI, XbaI and SmaI in the polylinker sequence respectively, T4 DNA polymerase treatment was performed to render the blunt end, which was followed by cleavage with SacI. Each fragment of HindIII/SacI, SphI/SacI, PstI/SacI, BamHI/SacI, XbaI/ SacI and SmaI/SacI, containing GUS gene was introduced into pBTF3(Sac) at the HincII/SacI site to construct each recombinant RNA3 transcription vector of pBTGUS(Hd)i (Sh), (Pt), (Sl), (Xa), (Bm) and (Sa) respectively (FIG. 4). Using these recombinant RNA3 transcription vectors, recombinants RNA3 were synthesized in vitro in a manner similar to example 1. B-1 and named tGUS(Hd), tGUS(Sh), tGUS(Pt), tGUS(Sl), tGUS(Xa), tGUS(Bm) and tGUS(Sa), respectively.

B. Construction of transcription vector (pBICGUS(Hc) for introducing recombinant RNA3) (FIG. 8)

Vector pBICGUS(Hc) was constructed to introduce into a plant genome recombinant BMV RNA3 GUS cDNA obtained by recombining a part of coat protein gene with GUS gene.

SmaI/SstI fragment containing GUS gene of pUCBI101 (FIG. 4) was introduced into a portion, from which the moiety between HincII site and SacI site cleaved by 6 base pairs from ATG translation initiation site of pBTF3(Sac) coat protein gene, to construct pBTGUS(Hc) wherein RNA3 cDNA coat protein gene has been replaced with GUS gene. XbaI/PthI fragment containing pBTGUS(Hc) GUS gene was introduced into a portion, from which the moiety between XbaI site and PthI site of RNA3 cDNA of transformation vector pBICBR3 (FIG. 6) has been removed, to construct pBICGUS(Hc).

C. Expression of GUS gene in a tobacco plant which produces 1a and 2a proteins

C-1. Analysis of GUS activity

The protoplast cultured for 48 hours after the inoculation was collected by centrifugation at 100×g for 2 minutes. To the protoplast was added 180 µl of dissolution buffer (50 mM phosphate buffer, pH 7.0, 10 mM EDTA, 0.1% Triton-X100, 0.1% Sarkosyl, 10 mM β-mercaptoethanol). After suspending them, the suspension was subjected to ultrasonic treatment at 15,000×g for 10 minutes to give about 180 µl of crude GUS protein extract. As substrate of GUS, 11 μl of 10 mM MUG (4-methylumbelliferyl glucuronide) was added to 45 μl of the extract. After reacting at 37° C. for 2 hour, 28 μl of 1M Na₂CO₃ was added to terminate the reaction. An amount of 4-MU (4-methylumbelliferone) produced was detected by fluorospectrophotometry (Gus gene fusion system user's manual).

C-2. Production of tobacco plant which produces 1a and 2a proteins

BR1 plant and BR2 plant, and BMR1 plant and BMR2 plant were hybridized, respectively. Hybridization was conducted by picking up the anther of blooming pollen parent BR1 plant with a pincette and pollinating the stigma of the mother R2 plant having removed stamen therefrom. About 4 weeks after, the seeds were harvested. Hybridization between BMR1 plant and BMR2 plant was conducted in a similar manner. The harvested seed were germinated on LS1 medium containing kanamycin (50 μg/ml) and kanamycin-resistant tobacco was selected. Since the plant in which both cDNAs of RNA1 and RNA2 has been introduced into the genome produces 1a and 2a proteins, coat protein can be produced by inoculating RNA3 on the protoplast. By the process in Example 2C, tobacco plant which produced coat protein was selected from the kanamycin-resistant tobacco plants. F1 plant of BR1 plant and BR2 plant, and F1 plant of BMR1 plant and BMR2 plant were named BR(1+2) and BMR(1+2), respectively. These are plants obtained by introducing both cDNAs of RNA1 and RNA2 into the genome and produce 1a and 2a proteins.

Next, in order to obtain the pure line diploid of BR(1+2) plant and BMR(1+2), anther culture was carried out by the method of Imamura et al. (Imamura et al., (1982), Plant cell Physiol, 23: 713–716). At the time when the second leaf of the resulting young haploid plant was out, the tip of the sprout was treated with 0.2% colchicine aqueous solution. The plants considered to be doubling ones were selected and those capable of producing coat protein were further selected in the process described in Example 2C. The plants were made pure line diploid. The pure line diploids obtained from BR(1+2) plant and BMR(1+2) plant were named BRP(1+2) plant and BMRP(1+2) plant, respectively.

C-3. Inoculation of recombinant RNA3 on tobacco protoplast which produces 1a and 2a proteins Each of recombinants RNA3 tGUS(Hd), tGUS(Sh), tGUS (Pt), tGUS(Sl), tGUS(Xa), tGUS(Bm) and tGUS(Sa), carrying GUS gene synthesized in vitro was inoculated on the protoplast prepared from BR(1+2) and BMR(1+2) plants. As negative control, each of tGUS(Hd), tGUS(Sh), tGUS(Pt), tGUS(Sl), tGUS(Xa), tGUS(Bm) and tGUS(Sa) alone was inoculated.

As the result, expression of GUS gene was confirmed in all of the BR(1+2) and BMR(1+2) inoculated with recombinant RNA3 carrying GUS gene. Amounts of the expression were in the order of tGUS(Sh), (Sa), (Pt), (Hd), (Xa), (Sl) and (Bm). The evaluation was made as follows, when an average value on the GUS activity in BR(1+2) plant tGUS(Sh) was made 100%.

|  | GUS Activity (%) |
|---|---|
| BR (1 + 2) plant inoculated with tGUS (Sh) | 100 |
| BR (1 + 2) plant inoculated with tGUS (Sa) | 98 |
| BR (1 + 2) plant inoculated with tGUS (Pt) | 98 |
| BR (1 + 2) plant inoculated with tGUS (Hd) | 96 |
| BR (1 + 2) plant inoculated with tGUS (Xa) | 93 |
| BR (1 + 2) plant inoculated with tGUS (Sl) | 93 |
| BR (1 + 2) plant inoculated with tGUS (Bm) | 93 |
| BR (1 + 2) plant | 0 |
| BMR (1 + 2) plant inoculated with tGUS (Sh) | 96 |
| BRM (1 + 2) plant inoculated with tGUS (Sa) | 93 |
| BMR (1 + 2) plant inoculated with tGUS (Pt) | 93 |
| BMR (1 + 2) plant inoculated with tGUS (Hd) | 95 |
| BMR (1 + 2) plant inoculated with tGUS (Xa) | 94 |
| BMR (1 + 2) plant inoculated with tGUS( Sl) | 93 |
| BMR (1 + 2) plant inoculated with tGUS (Bm) | 93 |
| BMR (1 + 2) plant | 0 |

C-4. Expression of the exogenous gene introduced into the genome of tobacco plant which produces 1a and 2a proteins In order to introduce into the genome of BRP(1+2) plant and BMPR(1+2) plant recombinant RNA3 cDNA obtained by recombining a part of coat protein gene with GUS gene, hybridization between BRP(1+2) plant and BR3GUS(Hc) plant, and between BMPR(1+2) plant and BR3GUS(Hc) plant was conducted, respectively. From the resulting F1 seeds, kanamycin-resistant seeds were selected. Further by the process in Example 3B-1, GUS activity was detected and the tobacco plants in which GUS gene was expressed were selected. The plant showing GUS activity among the F1 plants obtained by hybridization between BRP(1+2) plant and BR3GUS(Hc) plant was named BRP(1+2+3Ghc) plant, and the plant showing GUS activity among the F1 plants obtained by hybridization between BMRP(1+2) plant and BR3GUS(Hc) plant was named BMRP(1+2+3Ghc) plant, respectively.

In order to verify that the GUS activity in BRP(1+2+3GHc) plant and BMRP(1+2+3Ghc) plant is exhibited by GUS translated from recombinant RNA4 synthesized from recombinant RNA3 as a subgenome, Northern blot analysis was carried out using BRP(1+2+3Ghc) plant and BMRP(1+2+3Ghc) plant. The entire RNA (50 μg) from each of tobacco leaves was separated by agarose electrophoresis and transferred onto a nitrocellulose membrane. Then, the GUS activity was examined using pBI101 SmaI/SstI fragment containing GUS gene as a probe. A group of bands corresponding to the transcription product having the expected size of RNA4GUS showed an extremely strong hybridization. From the results, it was confirmed that recombinant RNA4 was synthesized in BRP(1+2+3Ghc) plant cells and BMRP(1+2+3Ghc) plant cells.

The evaluation was made as follows, when an average value on the activity of GUS activity in BRP(1+2+3Ghc) plant was made 100%.

|  | GUS Activity |
|---|---|
| BRP (1 + 2 + 3Ghc) plant | 100 |
| BRP (1 + 2) plant | 0 |
| BMRP (1 + 2 + 3Ghc) plant | 95 |
| BMRP (1 + 2) plant | 0 |

What is claimed is:

1. A process for production of an exogenous gene or its product in a plant cell which comprises:

inserting into a genome of a plant cDNA's of RNA1 and RNA2 replicase genes from brome mosaic virus, wherein said cDNA's have deletion of the nucleotides corresponding to the 3' terminal portion consisting of the nucleotide sequence extending from the 3' terminus to a site about 200 nucleotides in the 5' direction from said 3' terminus of virus RNA, and a cDNA of a recombinant brome mosaic virus genomic RNA3, wherein a coat protein gene is wholly or partly replaced with said exogenous gene which recombinant RNA3 molecule has an unmodified 3' terminus, or inoculating said recombinant virus genomic RNA on a plant cell having said cDNA's of RNA1 and RNA2 repilcase genes inserted in said genome.

2. A DNA molecule comprising a promoter which functions in a plant cell, cDNA's of RNA1 and RNA2 replicase genes of brome mosaic virus, wherein said cDNA's have deletion of the nucleotides corresponding to the 3' terminal portion consisting of the nucleotide sequence extending from the 3' terminus to a site about 200 nucleotides in the 5' direction from said 3' terminus of virus RNA, and a terminator which functions in a plant.

3. A transformation vector carrying a DNA molecule of claim 2.

4. A DNA molecule comprising a promoter which functions in a plant cell, cDNA of a recombinant brome mosaic virus genomic RNA3 in which a coat protein gene is wholly or partly replaced with a desired gene, which recombinant RNA3 molecule has unmodified 3' terminus of virus RNA, and a terminator which functions in a plant.

5. A transformation vector carrying a DNA molecule of claim 4.

6. A transformed plant cell containing a DNA molecule of claim 2 in the genome of a plant cell.

7. A plant obtained by regeneration of a cell according to claim 6.

8. A transformed plant cell containing a DNA molecule of claim 4 in the genome of a plant cell.

9. A plant obtained by regeneration of a cell according to claim 8.

10. A transformed plant cell containing a DNA molecule of claim 2 and a DNA molecule comprising a promoter which functions in a plant cell, cDNA of a recombinant virus genomic RNA3 in which a coat protein gene is wholly or partly replaced with a desired gene, which recombinant RNA3 molecule has an unmodified 3' terminus.

11. A plant obtained by regeneration of a cell according to claim 10.

12. A plant according to claim 7, wherein said plant belongs to the family selected from Leguminosae, Umbelliferae, Cruciferae, Cucurbitaceae, Solanaceae and Gramineae.

13. Plant according to claim 9, wherein said plant is selected from the group consisting of Leguminosae, Umbelliferae, Cruciferae, Cucurbitaceae, Solanaceae and Gramineae.

14. A transformed plant cell containing a DNA molecule of claim 2 in a plant genome.

15. A plant obtained by regeneration of a cell according to claim 14.

16. A plant according to claim 15, wherein said plant is selected from the group consisting of Leguminosae, Umbelliferae, Cruciferae, Cucurbitaceae, Solanaceae and Gramineae.

17. A plant according to claim 15, wherein said plant is a tobacco plant.

18. A process for producing a transgenic plant which comprises:

1) transforming a plant with an expression construct comprising cDNA's of RNA 1 and RNA2 replicase genes from brome mosaic virus, wherein said cDNA's have deletion of the nucleotides corresponding to the 3' terminal portion consisting of the nucleotide sequence extending from the 3' terminus to a site about 200 nucleotides in the 5' direction from said 3' terminus of virus RNA, and 2) co-transfecting or inoculating the transformed plant with an expression vector comprising cDNA encoding a recombinant brome mosaic virus RNA3 wherein a coat protein gene is wholly or partially replaced with said exogenous gene; which recombinant RNA3 molecule has an unmodified 3' terminus.

19. A process according to claim 18, wherein said plant is a tobacco plant.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTAGATGCAT ATAGTGAGTC GTATTAATTT A            31

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCTTAAATT AATACGACTC ACTATATGCA T            31

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTAGGCCTCT CCAAATGAAA TGAAC            25

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AAATTAATAC GACTCACTAT ATGCAT            26

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

-continued

```
ATGCATATAGTGAGTCGTATTAATTT                                                      26
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
ATAAGGAAGT  TCATTTCATT  TGGAGAGGAC  ACGC                                         34
```

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GTAGGCCTCTCCAAATGAAATGAAC                                                       25
```